United States Patent [19]

Kiyama et al.

[11] Patent Number: 5,877,368
[45] Date of Patent: Mar. 2, 1999

[54] METHOD FOR PRODUCING AROMATIC HYDROCARBONS

[75] Inventors: Kazuyoshi Kiyama, Yokohama; Takashi Tsunoda; Masatsugu Kawase, both of Kurashiki, all of Japan

[73] Assignee: Sanyo Petrochemical Co., Ltd., Tokyo, Japan

[21] Appl. No.: 750,874

[22] PCT Filed: May 31, 1995

[86] PCT No.: PCT/JP95/01059

§ 371 Date: Dec. 20, 1996

§ 102(e) Date: Dec. 20, 1996

[87] PCT Pub. No.: WO96/10548

PCT Pub. Date: Apr. 11, 1996

[30] Foreign Application Priority Data

Oct. 3, 1994 [JP] Japan ................................. 6-260923

[51] Int. Cl.⁶ ............................. G07C 15/00; G07C 2/00; G07C 2/52; C10G 35/06
[52] U.S. Cl. ...................... 585/418; 585/407; 585/413; 585/415; 585/417; 585/414; 208/135; 208/138; 208/140
[58] Field of Search ..................... 585/407, 413, 585/415, 417, 418, 419; 208/135, 138, 140

[56] References Cited

U.S. PATENT DOCUMENTS

| | | | |
|---|---|---|---|
| 3,756,942 | 9/1973 | Cattanach | 208/137 |
| 3,845,150 | 10/1974 | Yan et al. | 260/673.5 |
| 3,914,171 | 10/1975 | Schoennagel | 208/135 |
| 4,720,602 | 1/1988 | Chu | 585/407 |
| 4,851,602 | 7/1989 | Harandi et al. | 585/324 |
| 4,885,420 | 12/1989 | Martindale | 585/321 |
| 4,912,273 | 3/1990 | Harandi et al. | 585/322 |

FOREIGN PATENT DOCUMENTS

| | | |
|---|---|---|
| 63-14732 | 1/1988 | Japan . |
| 4-5712 | 2/1992 | Japan . |

*Primary Examiner*—Glenn Caldarola
*Assistant Examiner*—Thuan D. Dang
*Attorney, Agent, or Firm*—Birch, Stewart, Kolasch & Birch, LLP

[57] ABSTRACT

Disclosed is a method for producing aromatic hydrocarbons, which comprises contacting a light hydrocarbon feedstock comprising olefins and/or paraffins with a zeolite catalyst in a fixed-bed, adiabatic reactor containing a fixed catalyst bed comprised of the zeolite catalyst, to thereby effect a catalytic cyclization reaction of the light hydrocarbon feedstock, wherein the catalytic cyclization reaction is performed under conditions which satisfy the following requirements: (1) the zeolite catalyst has an initial stage-catalytic activity of 0.2 ($sec^{-1}$) or more in terms of the initial stage, first-order reaction rate constant of the decomposition of n-hexane catalyzed by the zeolite catalyst; (2) the catalyst bed has a temperature of from 450° C. to 650° C.; (3) the catalyst bed exhibits a temperature distribution with respect to the distance from an inlet to an outlet of the catalyst bed, wherein the temperature distribution has at least one maximum temperature value; and (4) the temperature of the outlet of the catalyst bed is ±40° C. relative to the temperature of the inlet of the catalyst bed. By the method of the present invention, not only can aromatic hydrocarbons be produced in high yield, but also the lowering of the catalytic activity is small, so that the production of aromatic hydrocarbons can be stably conducted for a prolonged period of time.

39 Claims, 6 Drawing Sheets

Average temperature (T) of catalyst bed = Space average value of time average temperature distribution

METHOD FOR PRODUCING AROMATIC HYDROCARBONS

BACKGROUND OF THE INVENTION

1. Field of the Invention

The present invention relates to a method for producing aromatic hydrocarbons from light hydrocarbons. More particularly, the present invention is concerned with a method for producing aromatic hydrocarbons from light hydrocarbons, which comprises supplying a light hydrocarbon feedstock comprising at least one member selected from the group consisting of olefins and paraffins to a fixed-bed, adiabatic reactor containing a fixed catalyst bed comprised of a zeolite catalyst, to thereby contact the light hydrocarbon feedstock with the zeolite catalyst in the fixed-bed, adiabatic reactor and effect a catalytic cyclization reaction of the light hydrocarbon feedstock, wherein the zeolite catalyst has a specific activity, and the catalytic cyclization reaction is conducted under specific temperature conditions with respect to the catalyst bed.

By the method of the present invention, not only can aromatic hydrocarbons be produced in high yield, but also a lowering of the catalytic activity is small, so that the production of aromatic hydrocarbons can be stably conducted for a prolonged period of time. The method of the present invention can be advantageously used in the petrochemical industry and in petroleum refining, especially in the production of aromatic compounds and high-octane gasolines.

2. Prior Art

Various methods are conventionally known in which aromatic hydrocarbons are produced using as a catalyst a zeolite, such as ZSM-5. For example, Examined Japanese Patent Application Publication No. 56-42639 (corresponding to U.S. Pat. No. 3,756,942) discloses a method in which aromatic hydrocarbons are produced from a hydrocarbon feedstock which is comprised of paraffins, olefins and/or naphthenes, each having 5 or more carbon atoms, and which has an aromatic hydrocarbon content of 15% by weight or less, using a ZSM-5 type zeolite catalyst. Examined Japanese Patent Application Publication No. 4-5712 discloses a method in which aromatic hydrocarbons are produced from a hydrocarbon feedstock containing saturated hydrocarbons having 4 or less carbon atoms, unsaturated hydrocarbons having 2 to 4 carbon atoms and a virgin naphtha in a specific amount ratio, using a ZSM-5 type zeolite catalyst.

Further, U.S. Pat. No. 3,845,150 discloses a process in which a hydrocarbon comprising 20 to 65% by weight of saturated hydrocarbons and 20 to 50% by weight of unsaturated hydrocarbons is contacted with a ZSM-5 type zeolite catalyst, so that the process involving the cyclization reaction (exothermic) of the unsaturated hydrocarbons and the cyclization reaction (endothermic) of the saturated hydrocarbons can be performed under heat balanced conditions, thereby producing aromatic hydrocarbons by an isothermal reaction.

Japanese Patent Application prior-to-examination Publication (kohyo) No. 3-503656 (corresponding to U.S. Pat. No. 4,851,602) discloses a method in which a hydrocarbon feedstock containing lower alkanes and lower alkenes is contacted with a fluidized bed of an acid type zeolite catalyst having medium pores in a first conversion zone, thereby obtaining a reaction mixture (effluent stream) containing aromatic hydrocarbon-rich higher aliphatic hydrocarbons, and the obtained reaction mixture is contacted with a fluidized bed of an acid type zeolite catalyst having medium pores in a second conversion zone, thereby obtaining a product which is rich in alkylated aromatic hydrocarbons and which contains gasolines having 5 or more carbon atoms.

Further, Unexamined Japanese Patent Application Laid-Open Specification No. 63-69888 (corresponding-to U.S. Pat. No. 4,720,602) discloses a method in which a hydrocarbon feedstock containing at least 50% by weight of $C_2$–$C_{12}$ aliphatic hydrocarbons is converted to aromatic compounds, using a crystalline zeolite catalyst having a specific activity.

Unexamined Japanese Patent Application Laid-Open Specification No. 63-14732 discloses a method in which aromatic hydrocarbons are produced from light hydrocarbons, using a ZSM-5 type zeolite catalyst containing zinc and having specific properties.

Unexamined Japanese Patent Application Laid-Open Specification No. 3-182592 (corresponding to U.S. Pat. No. 4,885,420) discloses a method in which a hydrocarbon feedstock containing olefins is subjected to a hydrogenation reaction using hydrogen and a hydrogenation catalyst and then, the resultant product is subjected to a dehydrocyclodimerization reaction in a reactor containing a dehydrocyclodimerization catalyst, to thereby obtain aromatic hydrocarbons.

However, in the above-mentioned conventional methods, when it is attempted to produce aromatic hydrocarbons by using a fixed-bed, adiabatic reactor (which is commercially most advantageous because it is not only simple in structure but also has high efficiency), problems arise such that the yield of desired aromatic hydrocarbon product becomes low, or coking vigorously occurs, so that it becomes difficult to stably perform the process for the production of desired aromatic hydrocarbons. Therefore, it has conventionally been considered to be impossible to stably produce desired aromatic hydrocarbons in high yield by using a fixed-bed, adiabatic reactor. For producing aromatic hydrocarbons in high yield, some attempts have heretofore been made. For example, in Unexamined Japanese Patent Application Laid-Open Specification No. 3-182592, a process has been proposed in which olefins contained in a feedstock are first subjected to hydrogenation and then, the feedstock is subjected to a dehydrocyclodimerization reaction for the production of aromatic hydrocarbons. This process, however, is disadvantageous in that it needs to be carried out in two stages. Further, in some of the conventionally proposed methods for producing aromatic hydrocarbons in high yield, it is disadvantageously necessary to use reactors having complicated structures (such as an isothermal reactor, a moving-bed reactor and a fluidized-bed reactor).

As mentioned above, U.S. Pat. No. 3,845,150 discloses a process in which a feedstock containing saturated hydrocarbons and unsaturated hydrocarbons in a specific weight ratio is used so as to enable the process to be carried out under heat balanced conditions. In this process, although almost no heat is supplied from an external source, aromatic hydrocarbons are produced in substantially the same yield as in the case of a method in which a large amount of heat is supplied to the reaction system. However, in this prior art reference, there is no description concerning a temperature distribution in the reaction system or how to conduct a stable operation in which a lowering of the catalytic activity which is caused due to occurrence of coking on the catalyst, is suppressed. The above-mentioned Japanese Patent Application prior-to-examination Publication (kohyo) No. 3-103656 discloses a method in which a hydrocarbon feedstock containing lower alkanes and lower alkenes in such a weight ratio as to maintain almost isothermal reaction conditions in the conversion zone, is used to obtain a product which is rich in alkylated aromatic hydrocarbons and contains gasolines having 5 or more carbon atoms. In this method, a fluidized-bed reactor (in which both the catalytic reaction and the regeneration of the catalyst can be continuously conducted) is used to thereby prevent a lowering of the catalytic activity due to occurrence of coking on the catalyst. However, the fluidized-bed reactor used in this method has a complicated structure, so that the cost becomes high.

SUMMARY OF THE INVENTION

The present inventors have made extensive and intensive studies with a view toward solving the above-mentioned problems of the prior art. As a result, it has unexpectedly been found that in the production of aromatic hydrocarbons from light hydrocarbons, wherein a light hydrocarbon feedstock comprising at least one member selected from the group consisting of olefins and paraffins is supplied to a fixed-bed, adiabatic reactor containing a fixed catalyst bed comprised of a zeolite catalyst, to thereby contact the light hydrocarbon feedstock with the zeolite catalyst in the fixed-bed, adiabatic reactor and effect a catalytic cyclization reaction of the light hydrocarbon feedstock, when a zeolite catalyst having a specific activity is used, and the catalytic cyclization reaction is conducted under specific temperature conditions with respect to the catalyst bed, not only can desired aromatic hydrocarbons be produced in high yield, but also a lowering of the catalytic activity is small, so that the production of the desired aromatic hydrocarbons can be stably conducted for a prolonged period of time. The present invention has been completed, based on the above finding.

It is, therefore, a primary object of the present invention to provide a method for producing aromatic hydrocarbons by contacting a light hydrocarbon feedstock comprising at least one member selected from the group consisting of olefins and paraffins with a zeolite catalyst in a fixed-bed, adiabatic reactor wherein the desired aromatic hydrocarbons can be produced in high yield and stably for a prolonged period of time.

The foregoing and other objects, features and advantages of the present invention will be apparent from the following detailed description and claims taken in connection with the accompanying drawings.

BRIEF DESCRIPTION OF THE DRAWINGS

In the accompanying drawings:

In FIGS. 5 and 6, like parts and portions are designated by like numerals or characters.

DETAILED DESCRIPTION OF THE INVENTION

Figure 1:
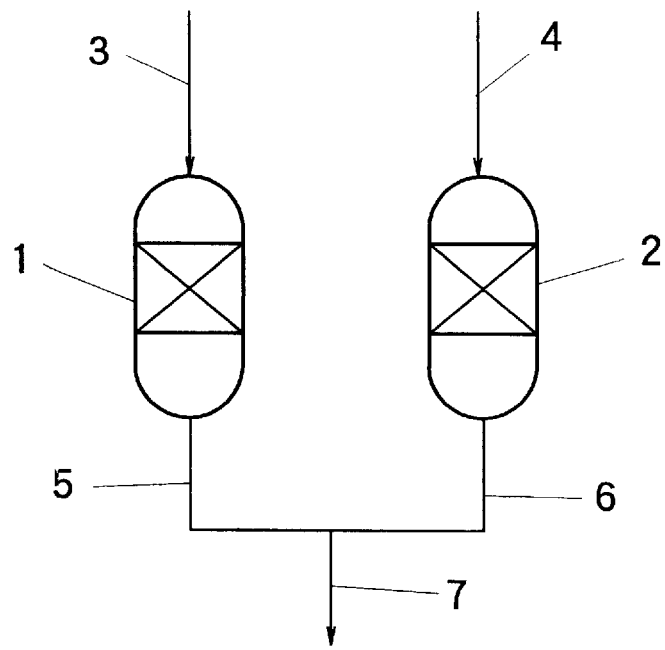
FIG. 1 is a flow sheet showing one mode of the method of the present invention.

Essentially, according to the present invention, there is provided a method for producing aromatic hydrocarbons from light hydrocarbons by catalytic cyclization, which comprises supplying a light hydrocarbon feedstock comprising at least one member selected from the group consisting of olefins and paraffins to a fixed-bed, adiabatic reactor containing a fixed catalyst bed comprised of a zeolite catalyst, to thereby contact the light hydrocarbon feedstock with the zeolite catalyst in the fixed-bed, adiabatic reactor and effect a catalytic cyclization reaction of the light hydrocarbon feedstock, the zeolite catalyst being at least one member selected from the group consisting of a substantially fresh zeolite catalyst and a steamed zeolite catalyst, wherein the catalytic cyclization reaction is performed under conditions which satisfy the following requirements (1), (2), (3) and (4):

(1) the zeolite catalyst has an initial stage-catalytic activity of 0.2 ($sec^{-1}$) or more in terms of the initial stage, first-order reaction rate constant of the decomposition of n-hexane catalyzed by the zeolite catalyst as measured at a temperature of 500° C. under atmospheric pressure;

(2) the catalyst bed has a temperature in the range of from 450° C. to 650° C.;

(3) the catalyst bed exhibits a temperature distribution with respect to the distance from an inlet of the catalyst bed to an outlet of the catalyst bed, wherein the temperature distribution has at least one maximum temperature value; and (4) the temperature of the outlet of the catalyst bed is in the range of ±40° C. relative to the temperature of the inlet of the catalyst bed.

In the present invention, the term "substantially fresh zeolite catalyst" is intended to mean not only a non-steamed zeolite catalyst, but also a zeolite catalyst which has been steamed to such an extent that a substantial modification of the zeolite catalyst has not been achieved. The term "substantial modification" means a modification in which the dealumination degree which is usually intended in the steaming of a zeolite catalyst is achieved.

For easy understanding of the present invention, the essential construction and various preferred embodiments of the present invention are enumerated below.

1. A method for producing aromatic hydrocarbons from light hydrocarbons by catalytic cyclization, which comprises supplying a light hydrocarbon feedstock comprising at least one member selected from the group consisting of olefins and paraffins to a fixed-bed, adiabatic reactor containing a fixed catalyst bed comprised of a zeolite catalyst, to thereby contact the light hydrocarbon feedstock with the zeolite catalyst in the fixed-bed, adiabatic reactor and effect a catalytic cyclization reaction of the light hydrocarbon feedstock, the zeolite catalyst being at least one member selected from the group consisting of a substantially fresh zeolite catalyst and a steamed zeolite catalyst, wherein the catalytic cyclization reaction is performed under conditions which satisfy the following requirements (1), (2), (3) and (4):

(1) the zeolite catalyst has an initial stage-catalytic activity of 0.2 ($sec^{-1}$) or more in terms of the initial stage, first-order reaction rate constant of the decomposition of n-hexane catalyzed by the zeolite catalyst as measured at a temperature of 500° C. under atmospheric pressure;

(2) the catalyst bed has a temperature in the range of from 450° C. to 650° C.;

(3) the catalyst bed exhibits a temperature distribution with respect to the distance from an inlet of the catalyst bed to an outlet of the catalyst bed, wherein the temperature distribution has at least one maximum temperature value; and (4) the temperature of the outlet of the catalyst bed is in the range of ±40° C. relative to the temperature of the inlet of the catalyst bed.

2. The method according to item 2 above, wherein the zeolite catalyst consists essentially of a zeolite.

3. The method according to item 1 above, wherein the zeolite catalyst comprises a mixture of a zeolite and at least one member selected from the group consisting of a metal belonging to Group VIII, Ib, IIb or IIIa of the Periodic Table and compounds thereof.

4. The method according to item 3 above, wherein the zeolite catalyst comprises a mixture of a zeolite and at least one member selected from the group consisting of zinc and compounds thereof.

5. The method according to item 4 above, wherein the zeolite catalyst comprises a mixture of a zeolite, at least one member selected from the group consisting of zinc and compounds thereof, and alumina.

6. The method according to item 4 above, wherein the zeolite catalyst comprises a mixture of a zeolite and a product obtained by heat-treating in steam a mixture of alumina and at least one member selected from the group consisting of zinc and compounds thereof.

7. The method according to item 4 above, wherein the zeolite catalyst comprises a mixture of a zeolite and zinc aluminate.

8. The method according to any one of items 4 to 7 above, wherein the content of the at least one member selected from the group consisting of zinc and compounds thereof in the zeolite catalyst is from 5 to 25% by weight in terms of the amount of zinc.

9. The method according to item 1 above, wherein the zeolite of the zeolite catalyst is substituted with a metal belonging to Group VIII, Ib, IIb or IIIa of the Periodic Table.

10. The method according to any one of items 1 to 9 above, wherein the zeolite of the zeolite catalyst has an Si/Al atomic ratio of at least 12 in the zeolite structure thereof, and has a sodium content of 500 ppm by weight or less.

11. The method according to any one of items 1 to 10 above, wherein the zeolite catalyst comprises a ZSM-5 zeolite.

12. The method according to any one of items 1 to 11 above, wherein the zeolite catalyst is a substantially fresh zeolite catalyst.

13. The method according to any one of items 1 to 11 above, wherein the zeolite catalyst is a steamed zeolite catalyst which is obtained by steaming a substantially fresh zeolite catalyst.

14. The method according to item 13 above, wherein the zeolite catalyst comprises a mixture of a steamed zeolite catalyst which has been obtained by steaming a substantially fresh zeolite catalyst consisting essentially of a zeolite, and at least one member selected from the group consisting of a metal belonging to Group VIII, Ib, IIb or IIIa of the Periodic Table and compounds thereof.

15. The method according to item 13 or 14 above, wherein the steaming of the substantially fresh zeolite catalyst is performed by flowing steam through a steaming reactor containing the substantially fresh zeolite catalyst in a sequence of the following steps (a) and (b):

(a) flowing steam having a steam partial pressure of at least 0.1 kg/cm² and a temperature of from 500° to 650° C. through the steaming reactor, to thereby contact the substantially fresh zeolite catalyst with the steam for 0.1 to 3 hours; and (b) temporarily stopping the flow of steam through the steaming reactor and removing the steam which remains in the reactor, whereupon steam having a steam partial pressure of 0.1 to 10 kg/cm² and a temperature of from 515° to 700° C. is flowed through the steaming reactor, with the proviso that the temperature of the steam flowed in step (b) is higher than the temperature of the steam flowed in step (a), wherein the step (b) is performed at least once, so that the steam individually flowed in the or each step (b) is brought into contact with the zeolite catalyst which has been steamed in the step preceding the or each step (b).

16. The method according to any one of items 1 to 15 above, wherein the light hydrocarbon feedstock comprises at least one member selected from the group consisting of a $C_4$ fraction of a product from a high temperature-thermal cracking system of a petroleum hydrocarbon material, or a fraction obtained by removing butadiene from or removing butadiene and i-butene from the $C_4$ fraction; a $C_5$ fraction of a product from a high temperature-thermal cracking system of a petroleum hydrocarbon material, or a fraction obtained by removing dienes from the $C_5$ fraction; thermally-cracked gasoline; a raffinate obtained by extracting aromatic hydrocarbons from thermally-cracked gasoline; FCC-LPG; FCC-cracked gasoline; a raffinate obtained by extracting aromatic hydrocarbons from reformate; coker LPG; and virgin naphtha.

17. The method according to any one of items 1 to 16 above, wherein the light hydrocarbon feedstock comprises a saturated hydrocarbon fraction and an unsaturated hydrocarbon fraction, and wherein the weight ratio of the saturated hydrocarbon fraction to the unsaturated hydrocarbon fraction is from 0.43 to 2.33.

18. The method according to any one of items 1 to 17 above, wherein the internal pressure of the adiabatic reactor during the cyclization reaction is in the range of from atmospheric pressure to 30 kg/cm²·G, and the light hydrocarbon feedstock is fed to the adiabatic reactor at a weight hourly space velocity (WHSV) of 0.1 to 50 $hr^{-1}$.

19. The method according to any one of items 1 to 18 above, which further comprises separating the resultant cyclization reaction mixture containing an aromatic hydrocarbon product into product A comprised mainly of the aromatic hydrocarbon product and product B comprised mainly of hydrogen and a non-aromatic hydrocarbon product having 1 to 5 carbon atoms, and wherein the separation is performed by means of a gas-liquid separator and optionally a distillation column.

20. The method according to any one of items 1 to 18 above, which further comprises separating the resultant cyclization reaction mixture containing an aromatic hydrocarbon product into product A comprised mainly of the aromatic hydrocarbon product, product C comprised mainly of a non-aromatic hydrocarbon product having 4 to 5 carbon atoms and product D comprised mainly of hydrogen and a non-aromatic hydrocarbon product having 1 to 3 carbon atoms, and wherein the separation is performed by means of a gas-liquid separator and optionally a distillation column.

21. The method according to item 19 or 20 above, wherein the gas-liquid separation is conducted using a coolant comprised of propylene or ethylene, and wherein the propylene or the ethylene are produced in and used as a coolant in a process for producing ethylene by a high temperature-thermal cracking of a petroleum hydrocarbon.

22. The method according to item 19 above, wherein at least part of the product B comprised mainly of hydrogen and a non-aromatic hydrocarbon product having 1 to 5 carbon atoms is recycled to the adiabatic reactor and used as a part of the light hydrocarbon feedstock.

23. The method according to item 19 above, wherein at least part of the product B comprised mainly of hydrogen and a non-aromatic hydrocarbon product having 1 to 5 carbon atoms is supplied to a high temperature-thermal cracking system of a petroleum hydrocarbon material.

24. The method according to item 20 above, wherein at least part of at least one member selected from the group consisting of the product C comprised mainly of a non-aromatic hydrocarbon product having 4 to 5 carbon atoms and the product D comprised mainly of hydrogen and a non-aromatic hydrocarbon product having 1 to 3 carbon atoms is recycled to the adiabatic reactor and used as a part of the light hydrocarbon feedstock.

25. The method according to item 20 above, wherein at least part of at least one member selected from the group consisting of the product C comprised mainly of a non-aromatic hydrocarbon product having 4 to 5 carbon atoms and the product D comprised mainly of hydrogen and a non-aromatic hydrocarbon product having 1 to 3 carbon atoms is supplied to a high temperature-thermal cracking system of a petroleum hydrocarbon.

26. The method according to any one of items 19 to 25 above, which further comprises processing the product A comprised mainly of the aromatic hydrocarbon product by at least one method selected from the group consisting of the following methods:
 a method in which the product A is processed using a dealkylation apparatus to thereby produce benzene;
 a method in which the product A is processed using a distillation apparatus, an extraction apparatus or an extractive distillation apparatus to thereby produce benzene, toluene and xylene;
 a method in which the product A is processed using a disproportionation apparatus or an isomerization apparatus; and
 a method in which the product A is blended with gasoline.

27. The method according to any one of items 1 to 26 above, which further comprises temporarily stopping the supply of the light hydrocarbon feedstock to the fixed-bed, adiabatic reactor, and burning off coke formed on the zeolite catalyst during the catalytic cyclization reaction with an oxygen-containing inert gas as a burning gas to regenerate the zeolite catalyst in a catalyst regeneration zone.

28. The method according to item 27 above, wherein an exhausted burning gas flowing out of the catalyst regeneration zone is recycled to the catalyst regeneration zone through a heater by means of a recycling compressor to thereby form a burning gas circulation system comprising the catalyst regeneration zone, the recycling compressor and the heater which are connected in this order through a pipeline, and wherein a fresh, oxygen-containing inert gas is supplied to the burning gas circulation system at a first port positioned between an outlet of the catalyst regeneration zone and an inlet of the heater in an amount of 0.05 to 50% by volume, based on the circulation volume of the burning gas, while discharging from the burning gas circulation system the exhausted burning gas flowing out of the catalyst regeneration zone before reaching the heater in an amount which is substantially equal to the amount of the fresh, oxygen-containing inert gas supplied to the first port, wherein the amount and oxygen content of the fresh, oxygen-containing inert gas supplied are adjusted, so that the burning gas flowing into the catalyst regeneration zone has an oxygen content of 0.01 to 10% by volume.

29. The method according to item 28 above, which further comprises supplying a fresh inert gas containing no oxygen to the burning gas circulation system at a second port, which is identical with the first port or is provided separately from the first port between the outlet of the catalyst regeneration zone and the inlet of the heater, in an amount of 10% by volume or less, based on the circulation volume of the burning gas, while incrementally discharging from the burning gas circulation system the exhausted burning gas flowing out of the catalyst regeneration zone before reaching the heater in an amount which is substantially equal to the amount of the fresh inert gas, containing no oxygen, supplied to the second port, thereby suppressing an increase in the partial pressure of steam in the burning gas flowing into the catalyst regeneration zone.

30. The method according to item 29 above, which further comprises cooling the burning gas to be compressed by means of the recycling compressor, and heating the compressed burning gas before reaching the heater, wherein the cooling and heating are conducted by means of at least one heat exchanger.

31. The method according to any one of items 13 to 15 above, wherein the steaming of the substantially fresh zeolite catalyst is performed using a steam circulation system including a steaming reactor, a recycling compressor, a heater and at least one heat exchanger, which are connected through a pipeline.

32. The method according to item 31 above, wherein the steaming reactor is used as the adiabatic reactor.

33. The method according to item 31 or 32 above, wherein the steam circulation system is utilized as the burning gas circulation system for the regeneration of the zeolite catalyst according to the method of item 30 above, wherein the steaming reactor is used as or replaced by a regeneration reactor comprising the catalyst regeneration zone in the burning gas circulation system, and wherein the burning gas for the burning gas circulation system is used in place of the steam for the steam circulation system.

The zeolite of the zeolite catalyst to be used in the method of the present invention has an Si/Al atomic ratio of from 2 to 60 in the zeolite structure thereof. Examples of zeolites usable in the method of the present invention include β-zeolite, Ω-zeolite, Y-zeolite, L-zeolite, erionite, offretite, mordenite, ferrierite, ZSM-5, ZSM-8, ZSM-11, ZSM-12, ZSM-35 and ZSM-38. Of these, crystalline aluminosilicates and crystalline metallosilicates of the ZSM-5 family, i.e., ZSM-5, ZSM-8 and ZSM-11, etc. are preferred. With respect to the details of zeolites of the ZSM-5 family, reference can be made to, for example, U.S. Pat. No. 5,268,162.

As a zeolite catalyst to be used in the present invention, a zeolite catalyst consisting essentially of a zeolite can be used. However, the zeolite catalyst to be used in the present invention can further comprise at least one metal selected from the metals belonging to Group VIII, Ib, IIb or IIIa of the Periodic Table. It is preferred that the zeolite catalyst comprise a mixture of a zeolite and at least one member selected from the group consisting of a metal belonging to Group VIII, Ib, IIb or IIIb of the Periodic Table and compounds thereof (e.g., a metal oxide, such as zinc oxide, which metal oxide is capable of promoting the dehydrogenation of the zeolite). Among the metals belonging to Group VIII, Ib, IIb or IIIa of the Periodic Table, a metal selected from Zn, Cu, Ag, Ni, Pt, Pd and Ga is preferred. Of these metals, Zn, Ag, Ni and Ga are especially preferred. For example, it is preferred that the zeolite catalyst comprise a mixture of a zeolite and at least one member selected from the group consisting of zinc and compounds thereof. More preferably, the zeolite catalyst further comprises alumina and silica as binders.

In the method of the present invention, examples of materials usable as at least one member selected from the group consisting of zinc and compounds thereof (hereinafter frequently referred to as a "zinc component") include zinc; zinc oxide; zinc hydroxide; salts, such as zinc nitrate, zinc carbonate, zinc sulfate, zinc chloride, zinc acetate and zinc oxalate; and organic zinc compounds, such as alkyl zinc.

In the method of the present invention, it is preferred that the zeolite catalyst comprise a mixture of a zeolite, a zinc component and alumina. It is also preferred that the zeolite catalyst comprise a mixture of a zeolite and a product obtained by heat-treating in steam a mixture of alumina and a zinc component. In either case, when the zeolite catalyst is steamed as described in detail below, the zinc component and the alumina react with each other to produce zinc aluminate in which the zinc is stabilized, so that the evaporation loss of the zinc under cyclization reaction conditions is largely reduced. Also, when the zeolite catalyst comprises a mixture of a zeolite and zinc aluminate, the same effects as mentioned above can be obtained. The zinc aluminate referred to herein means zinc aluminate which exhibits the same X-ray diffraction pattern as shown in JCPDS 5-0669 NBS Circ., 539, Vol. II, 38 (1953), when measured by an X-ray diffractometer, such as XD-610 manufactured and sold by Shimadzu Corporation, Japan.

In the method of the present invention, the alumina can be anhydrous alumina or hydrated alumina. Also, materials which are capable of producing anhydrous or hydrated alumina by hydrolysis, thermal decomposition, oxidation or the like thereof, can be used.

When the zeolite catalyst contains at least one member selected from the group consisting of zinc and compounds thereof, it is preferred that the content of the at least one member selected from the group consisting of zinc and compounds thereof in the zeolite catalyst be 5 to 25% by weight in terms of the amount of zinc.

When the zeolite catalyst contains alumina, the alumina content of the catalyst, in terms of $Al_2O_3$, is 5 to 50% by weight, preferably 20 to 40% by weight, based on the weight of the zeolite catalyst. When zinc is contained in addition to alumina, the molar ratio of alumina to zinc ($Al_2O_3/Zn$ molar ratio) is 1 or more.

The zeolite to be used in the present invention may be in an H form or in a metal-substituted form. In the case of the metal-substituted zeolite, a metal belonging to Group VIII, Ib, IIb or IIIa of the Periodic Table is preferred as a substituent. Among metals belonging to Group VIII, Ib, IIb or IIIa of the Periodic Table, a metal selected from Zn, Cu, Ag, Ni, Pt, Pd and Ga is preferred. Of these metals, Zn, Ag, Ni and Ga are especially preferred. Further, as mentioned above, the zeolite may be used in combination with a binder, such as alumina, and/or a metal oxide, such as zinc oxide, which metal oxide is capable of promoting the dehydrogenation of the zeolite. It is known that the activity of a zeolite varies depending on the content of sodium in the zeolite. It is preferred that the sodium content of the zeolite catalyst be relatively low, particularly 500 ppm by weight or less. Such a low sodium content is important especially when the Al zeolite has an Si/Al atomic ratio of 12 or more in the zeolite structure thereof.

In the present invention, the Si/Al atomic ratio means an Si/Al atomic ratio as measured by $^{29}Si$-NMR. With respect to the method for the measurement of the Si/Al atomic ratio by $^{29}Si$-NMR, reference can be made to "Jikken Kagaku Koza (Lecture On Experimental Chemistry) 5, NMR", 4th edition, p. 232–233, 1992, published by Maruzen Co., Ltd., Japan.

It is preferred that the zeolite catalyst to be used in the method of the present invention be a steamed zeolite catalyst which is obtained by steaming a substantially fresh zeolite catalyst. When a steamed zeolite catalyst is employed, the amount of coke substance accumulated on the surface of the zeolite catalyst during the subsequent catalytic cyclization reaction is reduced, thereby suppressing a lowering of the catalytic activity with time in the catalytic cyclization reaction.

For example, the above-mentioned steaming can be conducted at 500° to 800° C. for 0.1 to 50 hours under a steam partial pressure of 0.1 to 10 kg/cm. When a zeolite catalyst comprising a mixture of a zeolite, a zinc component and alumina is steamed by the above-mentioned method which is disclosed in Unexamined Japanese Patent Application Laid-Open Specification No. 2-115134, the zinc is stabilized, so that the evaporation loss of the zinc under the reaction conditions is largely reduced.

Examples of methods for obtaining a steamed zeolite catalyst comprising a mixture of a zeolite and other components, such as zinc, include (1) a method in which the above-mentioned mixture is first provided and, subsequently, the obtained mixture is steamed, (2) a method in which a steamed zeolite catalyst which has been obtained by steaming a substantially fresh zeolite catalyst consisting essentially of a zeolite is mixed with at least one member selected from the group consisting of a metal belonging to Group VIII, Ib, IIb or IIIb of the Periodic Table and compounds thereof and, optionally, another component (such as alumina or silica), and (3) a method in which the mixture obtained by the method (2) above is steamed again.

It is known that the stabilization of a zeolite by steaming is ascribed to the reaction (hereinafter referred to as "dealumination") in which aluminum in the zeolite is liberated from the zeolite structure by the action of steam. The heat of reaction generated in steaming a zeolite is large, and the dealumination rate of a zeolite is heavily dependent on the temperature. Therefore, when it is intended to conduct partial dealumination of a zeolite catalyst stably and uniformly on a commercial scale, it is extremely important to control the temperature of the catalyst during the steaming.

It is presumed that by steaming, the aluminum in a zeolite is liberated from the zeolite structure via the following reaction route:

(1) The partial dealumination proceeds in accordance with the reactions of the above two stages.

(2) The first-stage reaction is a reversible reaction, and, therefore, when the feeding of steam (H₂O) is stopped, the Al in the Al(H₂O)$_n$ as an intermediate is returned to the interior of the zeolite structure.

(3) The rate of the first-stage reaction is extremely high as compared to the rate of the second-stage reaction. The heat of reaction generated in the steaming is ascribed only to the first-stage reaction.

(4) The second-stage reaction is an irreversible reaction, and the reaction rate thereof is extremely-low as compared to the rate of the first-stage reaction.

As mentioned above, the heat of reaction generated by the first-stage reaction is large and the first-stage reaction proceeds very fast. Therefore, when steam is excessively fed to a catalyst bed in a reactor, the temperature of the catalyst bed is rapidly elevated over the entire region of the catalyst bed. Thereafter, the elevation of the temperature no longer occurs and the catalyst bed is cooled with steam or inert gas which continues to flow through the reactor.

Figure 4:
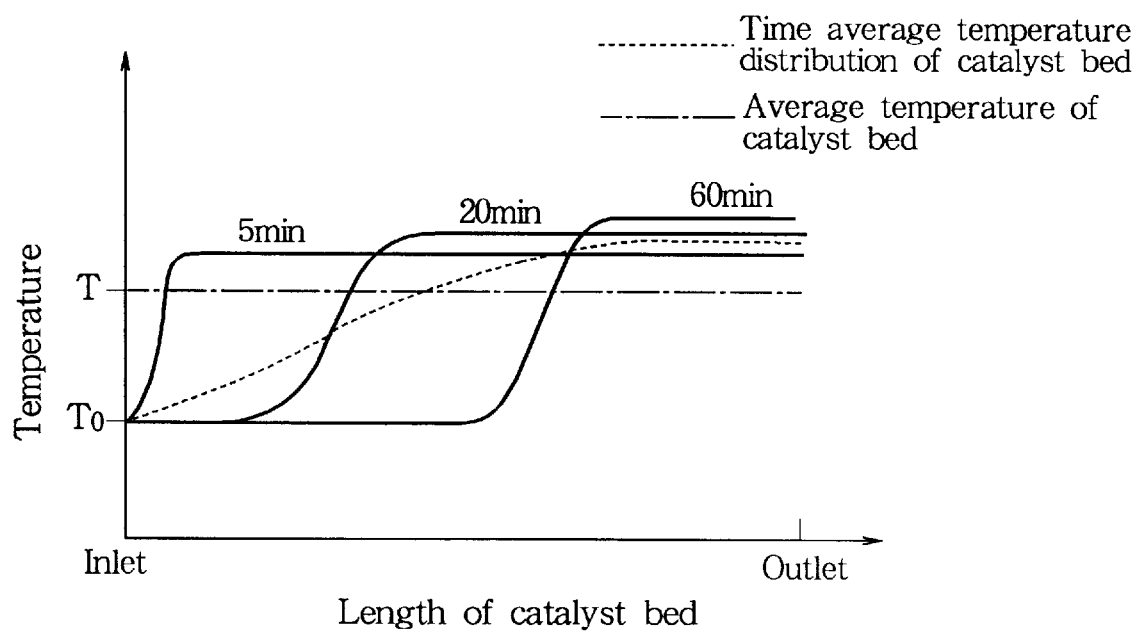
FIG. 4 is a diagram showing one preferred profile of uniform temperature distribution during the steaming of a catalyst bed comprising a zeolite catalyst to be used in the method of the present invention, shown together with a profile of non-uniform temperature distribution.

FIG. 4 is a diagram showing one preferred profile of uniform temperature distribution during the steaming of a catalyst bed comprising a zeolite catalyst to be used in the method of the present invention, shown together with a profile of non-uniform temperature distribution. In the case of the steaming method of FIG. 4, a fixed-bed, single-stage adiabatic reactor is used, and the steaming is conducted by feeding steam at a temperature of $T_0$ to the reactor from an upper portion thereof and flowing the steam through the reactor for 60 minutes. In FIG. 4, the solid lines show the respective temperature distributions in the reactor at predetermined points of time from the start of the feeding of steam, and the broken line shows the distribution of the time average temperatures of the respective blocks of the catalyst bed with respect to the period of time of from immediately after the start of the feeding of steam through 60 minutes after the start of the feeding of steam. When the steaming is conducted at a time average temperature distribution as indicated by the broken line in FIG. 4, the portion of the catalyst bed which is close to the inlet of the reactor, i.e., the portion of the catalyst bed which is first contacted by the fluid fed to the catalyst bed, becomes higher in activity than the portion of the catalyst bed which is close to the outlet of the reactor, thereby producing a non-uniform catalyst activity distribution after the steaming. That is, the average catalyst activity of the entire catalyst bed after being steamed at the time average temperature distribution as indicated by the broken line in FIG. 4 is equal to the catalyst activity which is exhibited by the catalyst bed after being steamed at a uniform temperature distribution [in which the temperature is equal to the average temperature of the catalyst bed (T) as indicated by the dot-and-dash line in FIG. 4], but, in the former case, where steaming is conducted at the time average temperature distribution as indicated by the broken line in FIG. 4, the catalyst bed exhibits a non-uniform distribution of catalytic activity. Therefore, when a catalyst bed which has been subjected to steaming at a time average temperature distribution as indicated by the broken line in FIG. 4 is used for, e.g., a catalytic cyclization reaction, there is a problem in that the catalyst bed undergoes vigorous coking at a portion close to the inlet of the reactor, so that a large deterioration of the catalyst due to coking occurs. For this reason, for obtaining a catalyst bed which has a high and stabilized catalytic activity over the entire area thereof, it is preferred that the steaming be conducted at a substantially uniform temperature distribution, such as is indicated by the dot-and-dash line in FIG. 4.

When the partial dealumination is conducted by a method in which the flowing of the steam is conducted in one stage, it is likely that a temperature difference would be produced between an upper portion of the catalyst bed and a lower portion of the catalyst bed as indicated by the solid line in FIG. 4, so that a uniform partial dealumination becomes difficult.

Therefore, in the present invention, it is advantageous that the flowing of the steam be conducted in 2 or more stages under the conditions described below.

Specifically, it is preferred that the steaming of the substantially fresh zeolite catalyst be performed by flowing steam through a steaming reactor containing the substantially fresh zeolite catalyst in a sequence of the following steps (a) and (b):

(a) flowing steam having a steam partial pressure of at least 0.1 kg/cm² and a temperature of 500° to 650° C. through the steaming reactor, to thereby contact the substantially fresh zeolite catalyst with the steam for 0.1 to 3 hours; and (b) temporarily stopping the flowing of the steam through the steaming reactor and removing the steam which remains in the reactor, whereupon steam having a steam partial pressure of 0.1 to 10 kg/cm² and a temperature of 515° to 700° C. is flowed through the steaming reactor, with the proviso that the temperature of the steam flowed in step (b) is higher than the temperature of the steam flowed in step (a), wherein the step (b) is performed at least once, so that the steam individually flowed in the or each step (b) is brought into contact with the zeolite catalyst which has been steamed in the step preceding the or each step (b).

In this preferred embodiment of the method of the present invention, the flowing of steam through the reactor is preferably conducted in 2 or more stages in such a manner as described below, so that the temperature difference between the upper portion and lower portion of the catalyst bed can be reduced, thereby enabling the steaming to be performed stably and uniformly.

In the first-stage operation (a) of the multistage steaming process according to this preferred embodiment of the invention, steam having a steam partial pressure of at least 0.1 kg/cm², preferably 0.5 to 1 kg/cm² and a temperature of 500° to 650° C., preferably 550° to 650° C., more preferably 600° to 620° C. is flowed through the reactor, to thereby contact the substantially fresh zeolite catalyst with the steam for 0.1 to 3 hours, preferably 0.1 to 1 hour.

Steam to be flowed through the reactor in step (a) has a steam partial pressure of at least 0.1 kg/cm². The steam may be diluted with an inert gas. In this case, the concentration of the diluted steam is preferably not less than 10% by volume, more preferably from 20 to 80% by volume. As an inert gas, a gas other than such gases (e.g., alcohols and ethers) as will generate H₂O when contacted with a zeolite, can be used, and nitrogen is especially preferred. The weight hourly space velocity (WHSV) of the steam to be flowed through the reactor is preferably set at a value such that the steam partial pressure does not become non-uniform in the catalyst bed and other problems, such as channeling or biased flowing of steam, do not occur. More specifically, it is preferred that the WHSV value be 0.01 to 10 hr$^{-1}$. When the steam temperature is lower than 500° C., the effect of suppressing the generation of the heat of reaction in the second-stage steaming (and in the steaming of any further subsequent stages) is hardly exerted. When the steaming is effected at temperatures higher than 650° C., the temperature of the catalyst bed rises extremely due to the heat of reaction generated by the steaming, so that problems occur such that a special material having a high corrosion resistance at high temperatures must disadvantageously be used for the reactor. Further, when the steaming time in the first-stage is too long, a broad distribution of temperature occurs in the catalyst bed due to the heat of reaction generated by the steaming and, hence, a non-uniformity is caused in the degree of dealumination in the catalyst bed, so that the distribution of catalytic activity after the steaming becomes non-uniform.

In the second-stage operation (b) of the multi-stage steaming process, first, the flowing of the steam through the reactor is temporarily stopped and the steam remaining in the reactor is purged with an inert gas as mentioned above having a temperature of 20° to 700° C., preferably 20° to 600° C. In this instance, it is preferred that not only must the average temperature of the catalyst bed be rendered equal to the temperature of the steam to be subsequently used in the second-stage steaming operation, but also the temperature distribution of the catalyst bed must be rendered uniform to a degree such that the difference between the maximum temperature and the minimum temperature is 10° C. or lower. When the steam remaining in the reactor is not removed after temporarily stopping the flow of steam, the dealumination of the zeolite catalyst is caused to advance by the action of the remaining steam, which is undesirable from the viewpoint of achieving uniform dealumination of the zeolite catalyst. After removal of the remaining steam, steam having a steam partial pressure of 0.1 to 10 kg/cm$^2$, preferably 0.5 to 1 kg/cm$^2$ and a temperature of 515° to 700° C., preferably a temperature which is within ±10° C. with respect to the maximum temperature of the catalyst bed which has been reached by the first-stage steaming, is flowed through the reactor to thereby contact the steam with the zeolite catalyst for 0.1 to 50 hours, preferably 0.1 to 20 hours.

The above-mentioned second-stage operation (b) may also be conducted twice or more. The heat of reaction which is generated by the steaming in the second-stage (b) is ¼ to ⅗ of the heat of reaction generated in the first-stage steaming (a) and, hence, the uniformity of the temperature in the catalyst bed in the second-stage steaming is higher than in the first-stage steaming, so that uniform partial dealumination of a zeolite catalyst can be stably conducted.

In the method of the present invention, a zeolite catalyst which has been partially dealuminated by the method disclosed in South African Patent Application No. 94/7674 (corresponding to International Patent Application Publication No. WO 95/09050) can be preferably used.

In the method of the present invention, a fixed-bed, adiabatic reactor is used. With respect to an adiabatic reactor, reference can be made to the description at pages 25 to 26 of "Kogyo Hanno Sochi (Industrial Reaction Apparatus)", edited by Kenji Hashimoto, (published by Baifukan Co., Ltd Japan, 1984). As examples of adiabatic reactors, there can be mentioned those of a fixed-bed type, a moving-bed type, and a fluidized-bed type. Of these, a fixed-bed, adiabatic reactor is used in the method of the present invention. As a fixed-bed, adiabatic reactor, an adiabatic reactor of a fixed-bed, single-stage type (in which a catalyst bed of only a single stage is provided) is preferred, but a heat exchanger-interposed, fixed-bed, multi-stage, adiabatic reactor can also be used (in which a catalyst bed is divided into a plurality of stages, and a heat exchanger is interposed between adjacent stages to supply heat to or remove heat from the respective stages). Since coking occurs on the catalyst during the reaction, it is preferred to employ a fixed-bed, single-stage adiabatic reactor of double-reactor column type in which the catalytic cyclization reaction can be conducted continuously by alternately using the columns while conducting the burning off of any coke on the catalyst contained in the idle column not being used for the catalytic cyclization reaction.

The term "light hydrocarbon feedstock comprising at least one member selected from the group consisting of olefins and paraffins" mentioned herein means those hydrocarbons which have two or more carbon atoms and have a 90% distillation temperature at 190° C. or lower. Examples of paraffins include ethane, propane, butane, pentane, hexane, heptane, octane and nonane. Examples of olefins include ethylene, propylene, butene, pentene, hexene, heptene, octene and nonene. In addition to these olefins and/or paraffins, the light hydrocarbon feedstock to be used may also contain cycloparaffins, such as cyclopentane, methylcyclopentane and cyclohexane; cycloolefins, such as cyclopentene, methylcyclopentene and cyclohexene; and/or dienes, such as cyclohexadiene, butadiene, pentadiene and cyclopentadiene.

The above-mentioned hydrocarbons may be used in the form of a mixture. The mixture may contain $N_2$, $CO_2$, CO or other inert gases as diluents. The mixture may further contain $H_2$ or $CH_4$ which are effective for suppressing occurrence of coking on the zeolite catalyst during the reaction. The content of the diluent in the mixture is preferably 20% by volume or less, more preferably 10% by volume or less. It is especially preferred that the weight ratio of saturated hydrocarbons to unsaturated hydrocarbons in the light hydrocarbon feedstock be from 0.43 to 2.33. The term "weight ratio of saturated hydrocarbons to unsaturated hydrocarbons" mentioned herein is intended to mean the weight ratio of saturated hydrocarbons to unsaturated hydrocarbons in the light hydrocarbon feedstock to be fed to the reactor. When, as described in detail below with reference to FIG. 9, the reaction product withdrawn from reactor (40) is separated into a desired aromatic hydrocarbon fraction and a non-aromatic hydrocarbon fraction (as unreacted feedstock and/or by-products) by means of purification and separation means (41), and the non-aromatic hydrocarbon fraction is recycled, the weight ratio of saturated hydrocarbons to unsaturated hydrocarbons means the weight ratio in mixture (44) of fresh feed (43) and recycled fraction (42).

Examples of hydrocarbon mixtures as feedstocks to be used in the method of the present invention include a mixture of the hydrocarbons mentioned above, a $C_4$ fraction of a product obtained by subjecting a petroleum hydrocarbon, such as naphtha, to thermal cracking at high temperatures, or a fraction obtained by removing butadiene or both butadiene and i-butene from the $C_4$ fraction; a $C_5$ fraction of a product obtained by subjecting a petroleum hydrocarbon to thermal cracking at high temperatures, or a fraction obtained by removing dienes from the $C_5$ fraction; thermally cracked gasoline; a raffinate obtained by extracting aromatic hydrocarbons from thermally cracked gasoline; fluid catalytic cracking (FCC)-produced liquefied petroleum gas (LPG); FCC-cracked gasoline; a raffinate obtained by extracting aromatic hydrocarbons from reformate; coker LPG; and virgin naphtha. Especially preferred mixtures are the $C_4$ fraction and $C_5$ fraction of a high-temperature thermal-cracking product from a petroleum hydrocarbon, such as naphtha; and fractions obtained by removing at least a part of butadiene, i-butene, isoprene, and cyclopentadiene from the $C_4$ and $C_5$ fractions. More preferred feedstocks are those in which the weight ratio of the $C_4$ fraction to the $C_5$ fraction is 3/7 to 7/3. The above-mentioned hydrocarbon mixtures may be used individually or in combination. The term "high-temperature thermal-cracking product" used herein means a product produced by means of a thermal-cracking apparatus to be used for a thermal-cracking process using a pipeline, which is called "steam cracking". Steam cracking is described in The Oil and Gas Journal, pp. 220–222, May 12, 1969.

The hydrocarbon feedstock to be used in the method of the present invention may contain impurities, such as oxygen-containing compounds, e.g., TBA (tert-butyl alcohol), methanol, or the like.

Figure 8:
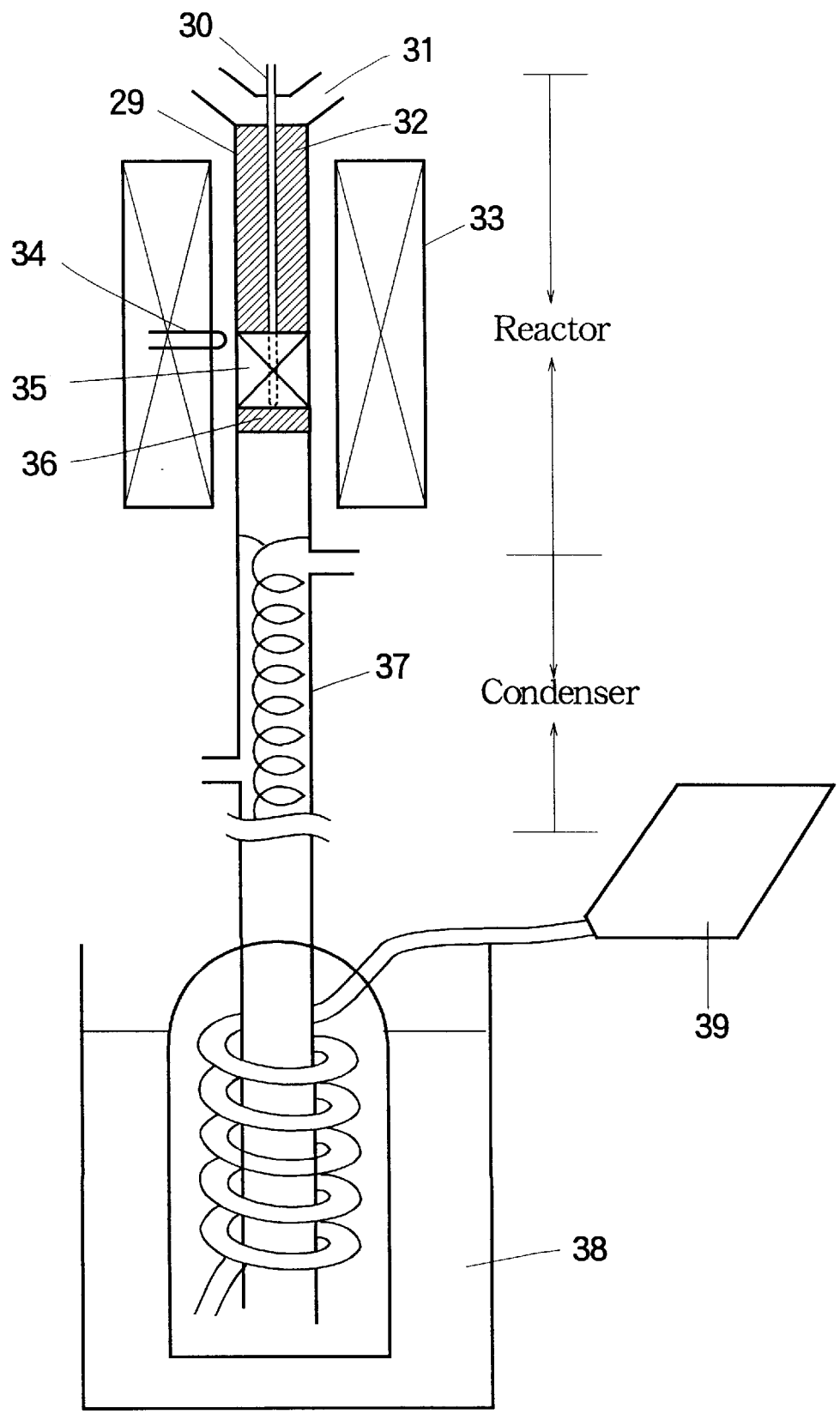
FIG. 8 shows a diagrammatic view of an isothermal reactor to be used for evaluation of the activity of a zeolite catalyst to be used in the method of the present invention.

In the present invention, the initial stage, first-order reaction rate constant of the decomposition of n-hexane catalyzed by a zeolite catalyst (hereinafter frequently referred to simply as "initial stage, first-order reaction rate constant of the decomposition of n-hexane") is obtained by a method in which a decomposition reaction of n-hexane is conducted, using the zeolite catalyst, in an apparatus shown in FIG. 8, and calculation is made using the volume value of the zeolite catalyst, the flow rate value of feedstock n-hexane and the concentration value of the n-hexane in the reaction product obtained. Illustratively stated, the initial stage, first-order reaction rate constant of the decomposition of n-hexane catalyzed by a zeolite catalyst is obtained as follows. Referring to FIG. 8, quartz reaction tube (29) (10 mmø) is packed with quartz wool (36), catalyst (35) and Raschig ring (32) in this order, from lower to upper portions of quartz reaction tube (29). Quartz reaction tube (29) is heated by means of electric furnace (33) provided with thermocouple (34) for adjusting the temperature, which furnace (33) enables the temperature of catalyst (35) contained in quartz reaction tube (29) to be constantly 500° C. as measured by thermometer (30). Then, n-hexane is fed to quartz reaction tube (29) from inlet (31) for feedstock through Raschig ring (32) under atmospheric pressure and at a weight hourly space velocity (WHSV) of 4 hr$^{-1}$. The reaction product obtained for a period of time between two time points of 0.75 hour and 1 hour each after the feeding of n-hexane (that is, 0.25 hour) is cooled with condenser (37), followed by further cooling with a coolant composed of dry ice and ethanol in oil trap (38). All the separated oil component in oil trap (38) and all the separated gaseous component in gas collector bag (39) are collected. The compositions of the obtained gaseous component and oil component are respectively analyzed by means of FID-TCD gas chromatography (HP-5890 Series II, manufactured and sold by Hewlett Packard Company, U.S.A.) and FID gas chromatography (GC-17A manufactured and sold by Shimadzu Corp., Japan), thereby obtaining the concentration value of n-hexane in the reaction product. The concentration value of n-hexane, the volume value of the zeolite catalyst and the flow rate value of feedstock n-hexane are respectively substituted for the corresponding items in the following formulae to obtain the average initial stage, first-order reaction rate constant of the decomposition of n-hexane with respect to the gas-oil collection time of 0.25 hour between two time points of 0.75 hour and 1 hour each after the feeding of n-hexane.

$$\text{average initial stage, first-order reaction rate constant of the decomposition of n-hexane with respect to the gas-oil collection time of 0.25 hour [hr}^{-1}] = \frac{1}{\theta} \times \ln \frac{100}{100 - (\text{n-hexane conversion})}$$

$$\theta [\text{hr}] = \frac{\text{volume of zeolite catalyst [m}^3]}{\text{flow rate of feedstock n-hexane [m}^3/\text{hr}]}$$

n-hexane conversion [%] = 100 − concentration of n-hexane in reaction product [wt %]

In the above formula for determining θ [hr], the term "volume of zeolite catalyst" is intended to mean the volume of the zeolite catalyst per se, which does not include the volume of inert substances (such as Rasching ring, glass beads, etc) contained in the catalyst bed. Thus, using the volume of the zeolite catalyst per se as "the volume of the zeolite catalyst", the initial stage, first-order reaction rate constant of the decomposition of n-hexane is obtained from the above formulae.

In the present invention, the initial stage, first-order reaction rate constant of the decomposition of n-hexane which is calculated using the above formulae and expressed in the unit (hr$^{-1}$) is used after the value has been converted into a value expressed in the unit (sec$^{-1}$).

In the method of the present invention, as mentioned above, it is requisite that the zeolite catalyst satisfy the following requirement (1):

(1) the zeolite catalyst has an initial stage-catalytic activity of 0.2 (sec$^{-1}$) or more in terms of the initial stage, first-order reaction rate constant of the decomposition of n-hexane catalyzed by the zeolite catalyst as measured at a temperature of 500° C. under atmospheric pressure.

When the zeolite catalyst has an initial stage-catalytic activity of less than 0.2 (sec$^{-1}$) in terms of the initial stage, first-order reaction rate constant of the decomposition of n-hexane, the yield of an aromatic hydrocarbon product becomes unsatisfactory. For conducting the production of an aromatic hydrocarbon product stably for a prolonged period of time, it is preferred that the initial stage-catalytic activity of the zeolite catalyst be 0.2 to 2 (sec$^{-1}$) in terms of the initial stage, first-order reaction rate constant of the decomposition of n-hexane. The term "the yield of an aromatic hydrocarbon product" used herein is intended to mean the yield of an aromatic hydrocarbon product, relative to the amount of non-aromatic hydrocarbons contained in the feedstock.

In the present invention, the term "temperature of the inlet of the catalyst bed" is intended to mean the temperature of the catalyst bed at the portion which is first contacted by the feedstock stream (the term "inlet of the catalyst bed" is hereinafter frequently referred to as "inlet of the reactor"). The term "temperature of the outlet of the catalyst bed" is intended to mean the temperature of the catalyst bed at the portion which is last contacted by the reaction mixture stream (the term "outlet of the catalyst bed" is hereinafter frequently referred to as "outlet of the reactor"). The term "temperature of the catalyst bed" is intended to mean the temperature of the catalyst bed measured at its portion corresponding to a portion of a plane perpendicular to the flow direction of the feed-stock stream, which portion of the plane is positioned at a distance of 0 to 0.8 d from the center of the plane, wherein d represents the distance between the center of the plane and the inner wall surface of the reactor. In the present invention, the term "maximum temperature value" of the temperature distribution of the catalyst bed with respect to the distance from an inlet of the catalyst bed to an outlet of the catalyst bed is intended to mean the maximum temperature value of a temperature distribution curve obtained by measuring temperatures over the entire region of from the inlet of the catalyst bed to the outlet of the catalyst bed. The term "maximum value" mentioned herein is intended to mean a maximum value in a purely mathematical aspect such as described in pages 56–57 of "Kaiseki Gairon (Generalities of Analysis)" edited by Yukinari Togi (published in 1983 by Gakujutsu Tosho Shuppan Publishing, Japan).

In the method of the present invention, the lower limit temperature of the catalyst bed is 450° C. or more, and the upper limit temperature of the catalyst bed is 650° C. or less.

In the present invention, the lowest temperature value of a temperature distribution curve obtained by measuring temperatures over the entire region of from an inlet of the catalyst bed to an outlet of the catalyst bed is defined as the lowest temperature value of the temperature distribution of the catalyst bed. The highest temperature value of a temperature distribution curve obtained by measuring temperatures over the entire region of from an inlet of the catalyst bed to an outlet of the catalyst bed is defined as the highest temperature value of the temperature distribution of the catalyst bed.

The temperatures of the catalyst bed, including the temperature of the inlet and outlet of the catalyst bed, are measured by means of a thermoelectric thermometer described at pages 384 to 389 of "Enerugii Kanri Gijutsu [Netsu Kanri-hen] (Energy Control Techniques [Heat Control])" edited by the committee for the edition of "Energy Control Techniques [Heat Control]" (published in 1989 by Energy Saving Center, Japan).

In the present invention, aromatic hydrocarbons are produced, using a zeolite catalyst having a catalytic activity satisfying requirement (1) mentioned above, under reaction conditions satisfying requirements (2) to (4) mentioned below:

(2) the catalyst bed has a temperature in the range of from 450° C. to 650° C.;

(3) the catalyst bed exhibits a temperature distribution with respect to the distance from an inlet of the catalyst bed to an outlet of the catalyst bed, wherein the temperature distribution has at least one maximum temperature value; and (4) the temperature of the outlet of the catalyst bed is in the range of ±40° C. relative to the temperature of the inlet of the catalyst bed.

Figure 3:
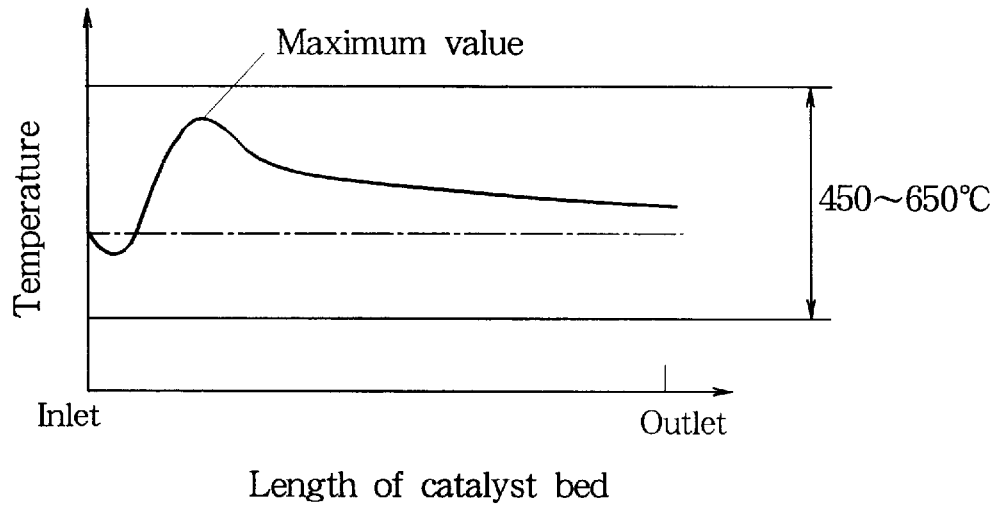
FIG. 3 is a diagram showing one preferred profile of temperature distribution in the catalyst bed used in the method of the present invention.

According to the method of the present invention, aromatic hydrocarbons can be produced in high yield and stably in a fixed-bed, adiabatic reactor. When the zeolite catalyst has an activity satisfying the above-mentioned requirement (1) and, in addition, the temperature conditions of the catalyst bed in the fixed-bed, adiabatic reactor satisfy the above-mentioned requirements (2) to (4), the production of aromatic hydrocarbons can be conducted in high yield and stably for a prolonged period of time with reduced coking. According to the above-mentioned requirements (2) to (4), it is requisite that, as shown in FIG. 3, the catalyst bed have a temperature in the range of from 450° C. to 650° C., preferably 490° C. to 600° C., more preferably 500° C. to 580° C., that the temperature distribution of the catalyst bed have at least one maximum value, and that the outlet temperature of the catalyst bed be in the range of ±40° C. relative to the inlet temperature of the catalyst bed. It is preferred that the catalyst bed have the at least one maximum temperature value at a position between the inlet of the catalyst bed and a portion of the catalyst bed at which the weight hourly space velocity (WHSV) of the feedstock is 4 hr$^{-1}$. It is more preferred that the catalyst bed have the at least one maximum temperature value at a position between a portion of the catalyst bed at which the WHSV of the feedstock is 80 hr$^{-1}$ and a portion of the catalyst bed at which the WHSV of the feedstock is 4.5 hr$^{-1}$. The temperature distribution of the catalyst bed in an isothermal reactor or the like has no maximum temperature value. When the outlet temperature of the catalyst bed is lower than −40° C. relative to the inlet temperature of the catalyst bed, the yield of the aromatic hydrocarbon is low. On the other hand, when the outlet temperature of the catalyst bed is higher than +40° C. relative to the inlet temperature of the catalyst bed, the temperature of the reaction zone becomes too high, so that coking is increased and the activity of the catalyst becomes rapidly lowered, thereby making it difficult to conduct a stable reaction. When the temperature of the catalyst bed is lower than 450° C., the yield of the aromatic hydrocarbon is low. On the other hand, when the temperature of the catalyst bed is higher than 650° C., coking is increased and the activity of the catalyst becomes rapidly lowered, thereby making it difficult to conduct a stable reaction.

When the zeolite catalyst satisfies the above-mentioned requirement (1) and, in addition, the temperature of the catalyst bed in the fixed-bed, adiabatic reactor satisfies the above-mentioned requirements (2) to (4), coking can be reduced and the production of an aromatic hydrocarbon can be conducted in high yield and stably for a prolonged period of time, as compared to the case of a reaction method in which any one of the above-mentioned requirements (1) to (4) is not satisfied.

Hereinbelow, preferred embodiments of the method of the present invention are described with reference to FIGS. 1 and 2.

Figure 2:
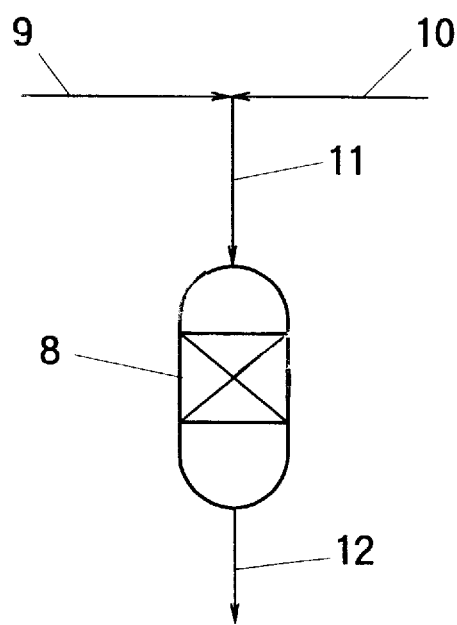
FIG. 2 is a flow sheet showing another mode of the method of the present invention.

In FIGS. 1 and 2, each of numerals 1 and 2 designates a fixed-bed, adiabatic reactor for producing aromatic hydrocarbons from light hydrocarbons. Into fixed-bed, adiabatic reactor 1 is fed feedstock stream 3 comprised of, for example, a C$_4$ fraction of a product from a high temperature-thermal cracking system of a petroleum hydrocarbon, such as naphtha, or a fraction obtained by removing butadiene or butadiene and i-butene from the C$_4$ fraction. Into fixed-bed, adiabatic reactor 2 is fed feedstock stream 4 comprised of, for example, a C$_5$ fraction of a product from a high temperature-thermal cracking system of a petroleum hydrocarbon, such as naphtha, or a fraction obtained by removing dienes from the C$_5$ fraction. The weight ratio of feedstock stream 3 and feedstock stream 4 is not particularly limited. For example, feedstock stream 3 at 4500° to 650° C. is fed into fixed-bed, adiabatic reactor 1 at a weight hourly space velocity (WHSV) of 0.1 to 50 hr$^{-1}$ under a pressure of from atmospheric pressure to 30 kg/cm$^2$·G. Feedstock stream 4 at the same temperature as feedstock stream 3 is fed into fixed-bed, adiabatic reactor 2 at the same weight hourly space velocity (WHSV) as in the feeding of feedstock stream 3 into fixed-bed, adiabatic reactor 1, under the same pressure as in the feeding of feedstock stream 3 into fixed-bed, adiabatic reactor 1. Reaction mixture streams 5 and 6, which are, respectively, formed in adiabatic reactors 1 and 2, are mixed with each other to form reaction mixture stream 7.

In FIG. 2, numeral 8 designates a fixed-bed, adiabatic reactor which is the same as each of adiabatic reactors 1 and 2 shown in FIG. 1. Feedstock stream 9 is the same as feedstock stream 3 shown in FIG. 1, and feedstock stream 10 is the same as feedstock stream 4 shown in FIG. 1. Feedstock streams 9 and 10 are mixed in the same weight ratio as used for feeding feedstock streams 3 and 4 in the embodiment shown in FIG. 1, to thereby form feedstock stream 11. Feedstock stream 11 is fed into fixed-bed, adiabatic reactor 8 at the same feedstock temperature, the same weight hourly space velocity (WHSV) and the same pressure as in the respective feeding of feedstock streams 3 and 4 to fixed-bed, adiabatic reactors 1 and 2 in the embodiment shown in FIG. 1.

In the method of the present intention, the yield of an aromatic hydrocarbon obtained by the embodiment described above with reference to FIG. 2 is likely to be higher than the yield of an aromatic hydrocarbon obtained by the embodiment described above with reference to FIG. 1.

The method of the present invention is not limited to the above embodiments.

In the present invention, it is preferred that the internal pressure of the fixed-bed, adiabatic reactor during the cyclization reaction be in the range from atmospheric pressure to 30 kg/cm$^2$·G, and the light hydrocarbon feedstock be fed to the adiabatic reactor at a weight hourly space velocity (WHSV) of 0.1 to 50 hr$^{-1}$.

The above-mentioned "internal pressure" of the reactor is intended to mean an average of the respective internal pressures at the inlet of the reactor and at the outlet of the reactor. The measurement of the internal pressure at each of the inlet and outlet of the reactor can be conducted by means of a pressure gauge described at pages 398 to 406 of "Enerugii Kanri Gijutsu [Netsu Kanri-hen] (Energy Control Techniques [Heat Control])" edited by the committee for the edition of "Energy Control Techniques [Heat Control]" (published in 1989 by Energy Saving Center, Japan).

The above-mentioned "weight hourly space velocity (WHSV)" is calculated using the following formula:

WHSV(hr$^{-1}$)=flow rate of feedstock stream (g/hr)/amount of catalyst (g)

The flow rate of the feedstock stream in the above formula can be measured by means of a flow meter described at pages 408 to 414 of the above-mentioned "Enerugii Kanri Gijutsu [Netsu Kanri-hen] (Energy Control Techniques [Heat Control])" edited by the committee for the edition of "Energy Control Techniques [Heat Control]" (published in 1989 by Energy Saving Center, Japan).

In the method of the present invention, the reaction mixture which is rich in an aromatic hydrocarbon product can be separated into a fraction comprised mainly of an aromatic hydrocarbon product and a fraction comprised mainly of a non-aromatic hydrocarbon product, by means of a gas-liquid separator and optionally a distillation column, as described below. In this case, the former fraction comprised mainly of an aromatic hydrocarbon product may be used as such, or may be subjected to treatments, such as dealkylation. With respect to the latter fraction comprised mainly of a non-aromatic hydrocarbon product, it is preferred that the fraction be recycled or supplied to other processes.

Hereinbelow, referring to the accompanying drawings showing preferred embodiments of the present invention, the method of the present invention is described in more detail.

Figure 5:
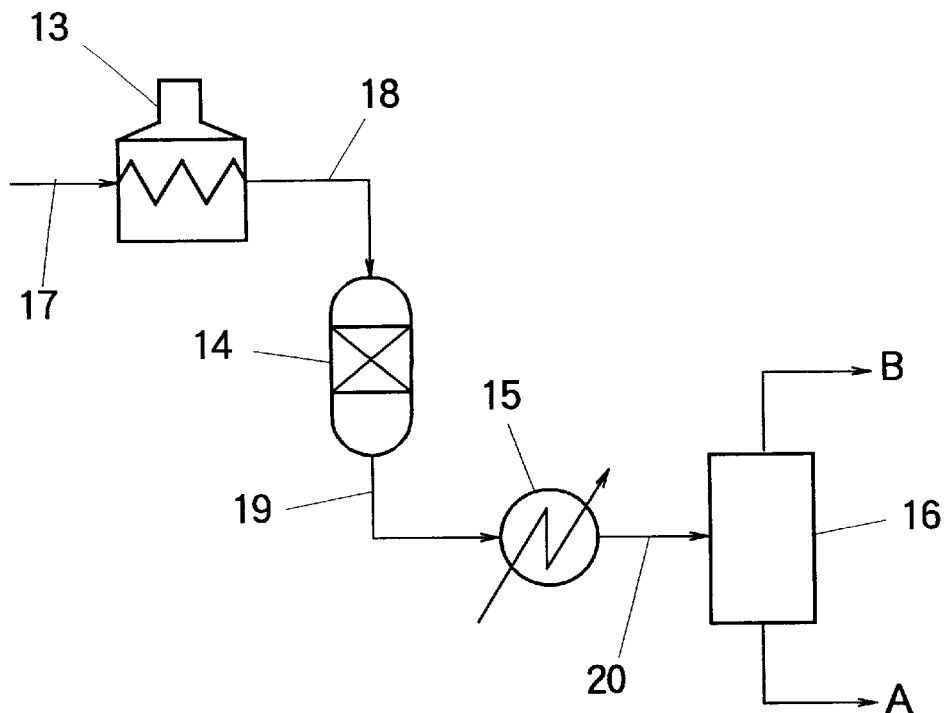
FIG. 5 is a flow sheet showing one mode of the separation of a reaction mixture obtained by the method of the present invention.

FIG. 5 is a flow sheet showing one mode of the separation of the reaction mixture obtained by the method of the present invention. In FIG. 5, feedstock stream 17 is heated in heater 13, and heated feedstock stream 18 is fed to fixed-bed, adiabatic reactor 14 containing a zeolite catalyst, to thereby obtain reaction mixture stream 19. Feedstock stream 17 is a light hydrocarbon feedstock comprising at least one member selected from the group consisting of olefins and paraffins. Specific examples of light hydrocarbon feedstocks include a $C_4$ fraction of a product from a high temperature-thermal cracking system of a petroleum hydrocarbon, such as naphtha, or a fraction obtained by removing butadiene or both butadiene and i-butene from the above-mentioned $C_4$ fraction; a $C_5$ fraction of a product from a high temperature-thermal cracking system of a petroleum hydrocarbon, or a fraction obtained by removing dienes from the above-mentioned $C_5$ fraction; thermally cracked gasoline; a raffinate obtained by extracting aromatic hydrocarbons from thermally cracked gasoline; FCC-LPG; FCC-cracked gasoline; a raffinate obtained by extracting aromatic hydrocarbons from reformate; coker LPG; and virgin naphtha. The heat of reaction mixture stream 19 may be utilized for preheating of feedstock stream 17.

Reaction mixture stream 19 is cooled by means of heat exchanger 15 for cooling, and cooled reaction mixture stream 20 is separated into product A comprised mainly of a desired aromatic hydrocarbon product and product B as a by-product comprised mainly of hydrogen and a non-aromatic hydrocarbon product (including paraffins, olefins and/or naphthenes having 1 to 5 carbon atoms), utilizing the boiling point difference between product A and product B, by means of separating means 16 including a gas-liquid separator and optionally a distillation column (which can improve the purity of the product separated by the gas-liquid separator). As mentioned above, for example, reaction mixture stream 19 may be cooled by means of heat exchanger 15 for cooling, or may be cooled by means of feedstock stream 17 and further cooled by means of heat exchanger 15 for cooling.

Figure 6:
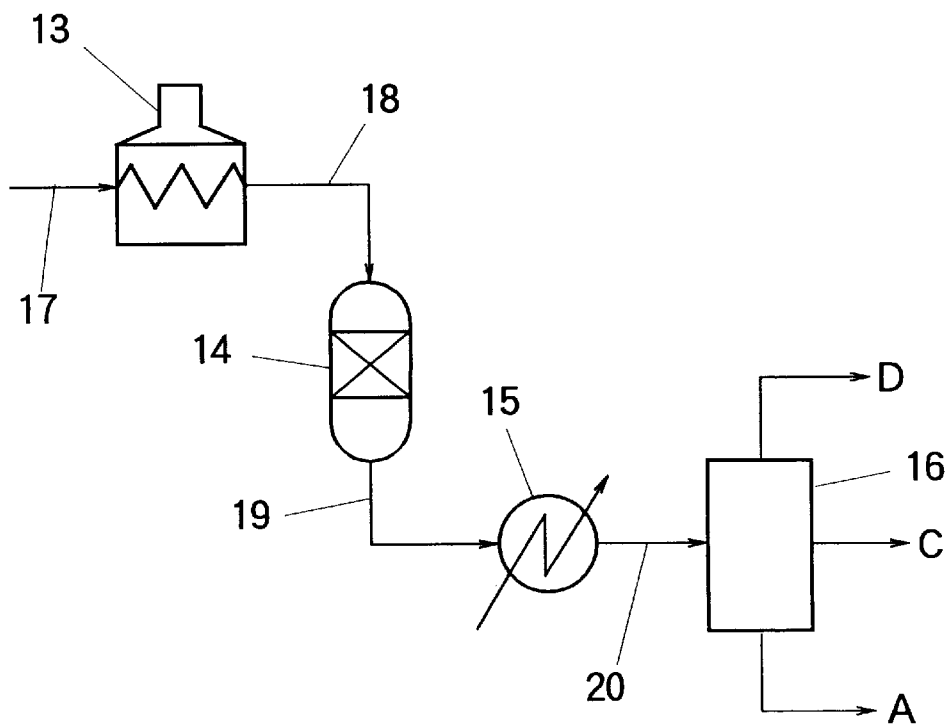
FIG. 6 is a flow sheet showing another mode of the separation of a reaction mixture obtained by the method of the present invention.

FIG. 6 is a flow sheet showing another mode of the separation of the reaction mixture obtained by the method of the present invention. As shown in FIG. 6, reaction mixture stream 19 is produced from feedstock stream 17 in the same manner as shown in FIG. 5. Reaction mixture stream 19 is cooled by means of heat exchanger 15 for cooling or may be cooled by means of feedstock stream 17 and further cooled by means of heat exchanger 15 for cooling. Cooled reaction mixture stream 20 is separated into product A comprised mainly of a desired aromatic hydrocarbon product, product C as a by-product comprised mainly of a non-aromatic hydrocarbon product having 4 to 5 carbon atoms and product D as a by-product comprised mainly of hydrogen and a non-aromatic hydrocarbon product having 1 to 3 carbon atoms, utilizing boiling point differences among products A, C and D, by means of separating means 16 including a gas-liquid separator and optionally a distillation column. The composition of product A comprised mainly of an aromatic hydrocarbon product shown in FIG. 5 may or may not be the same as the composition of product A comprised mainly of an aromatic hydrocarbon product shown in FIG. 6.

Examples of coolants which can be used in heat exchanger 15 for cooling shown in FIGS. 5 and 6 include cooling water, propylene, ethylene and fluorine compounds. For reducing the necessary equipment investment and required energy, a coolant comprised of propylene or ethylene, which is produced in and used as a coolant in a process for producing ethylene by a high temperature-thermal cracking of a petroleum hydrocarbon into ethylene and by-products including propylene and $C_4$ and $C_5$ fractions, can be used. In such a case, the by-products of the ethylene production process including $C_4$ and $C_5$ fractions can be used as at least a part of the light hydrocarbon feedstock.

In the present invention, feedstock stream 17 may be a $C_5$ fraction which has been obtained by a method in which a product from a high-temperature thermal cracking system of a petroleum hydrocarbon is supplied to a separator for a thermally cracked gasoline to obtain a thermally cracked gasoline, and the obtained thermally cracked gasoline is supplied to a separator for a $C_5$ fraction. In this case, as separating means 16 for separating reaction mixture stream 19, the above-mentioned separator for the $C_5$ fraction can be used.

In the present invention, the term "gas-liquid separator" is intended to mean those which are described at pages 73 to 130 of "Purosesu Kiki Kouzou Sekkei Shiriizu 2 Tousou-rui (Structural Design of Process Equipments, Series 2, Columns and Vessels)" edited by Kagaku Kougaku Kyokai (Society of Chemical Engineering) published in 1970 by Maruzen Co., Ltd., Japan. The term "distillation column" is intended to mean those which are described at pages 2 to 4 of "Purosesu Kiki Kouzou Sekkei Shiriizu 2 Tousou-rui (Structural Design of Process Equipments, Series 2, Columns and Vessels)" edited by Kagaku Kougaku Kyokai (Society of Chemical Engineering) published in 1970 by Maruzen Co., Ltd., Japan. The term "heater" is intended to mean tubular heaters which are described at pages 1 to 4 of "Purosesu Kiki Kouzou Sekkei Shiriizu 4 Kanetsuro (Structural Design of Process Equipments, Series 4, Heaters)" edited by Kagaku Kougaku Kyokai (Society of Chemical Engineering) published in 1970 by Maruzen Co., Ltd., Japan.

In the method of the present invention, at least part of product B comprised mainly of hydrogen and a non-aromatic hydrocarbon product having 1 to 5 carbon atoms, or at least part of at least one member selected from the group consisting of product C comprised mainly of a non-aromatic hydrocarbon product having 4 to 5 carbon atoms and product D comprised mainly of hydrogen and a non-aromatic hydrocarbon product having 1 to 3 carbon atoms (which products B, C and D are obtained by purification and separation of the desired aromatic hydrocarbon product), can be recycled to adiabatic reactor 14 and used as a part of the light hydrocarbon feedstock. In this case, the recycled product can be mixed with feedstock stream 17, or with feedstock stream 18 which is obtained by heating feedstock stream 17 by means of heater 13. Alternatively, the recycled product can be directly fed to a middle portion of the catalyst bed in reactor 14 instead of the inlet of reactor 14 in a manner such that the temperature conditions of the catalyst bed of reactor 14 satisfy the above-mentioned requirements (2) to (4).

Figure 9:
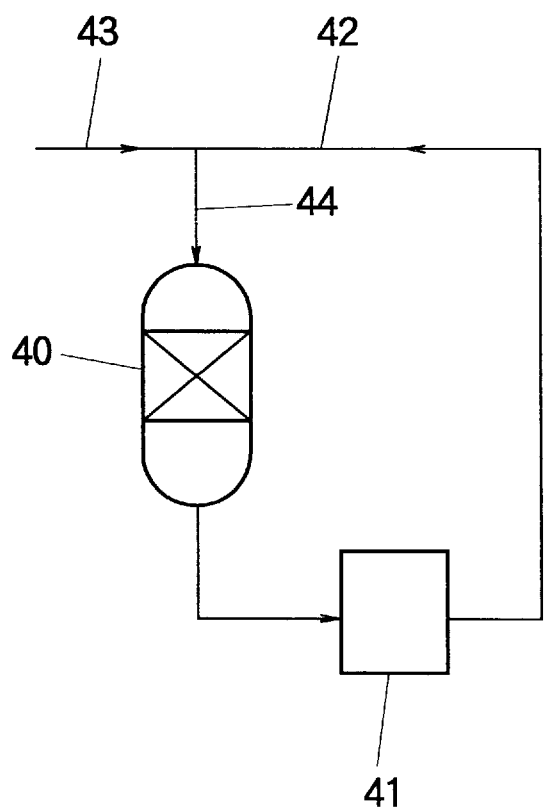
FIG. 9 is a flow sheet showing one mode of the recycling of a reaction product obtained by the method of the present invention.

A typical example of an embodiment in which, as mentioned above, at least part of product B or at least part of at least one member selected from the group consisting of products C and D is recycled to the reactor in the method of the present invention, is shown in FIG. 9. Illustratively stated, referring to FIG. 9 (which is a flow sheet showing one mode of the recycling of the reaction product obtained in the method of the present invention), fresh feed 43 is supplied to reactor 40 to obtain a reaction product, and the obtained reaction product is separated into a desired aromatic hydrocarbon product and a non-aromatic hydrocarbon product (as an intact feedstock or a by-product) by means 41 for purification and separation. The non-aromatic hydrocarbon product is recycled, and recycled product 42 is mixed with fresh feed 43 to obtain mixture 44, and mixture 44 is supplied to reactor 40.

Further, in the method of the present invention, at least part of product B comprised mainly of hydrogen and a non-aromatic hydrocarbon product having 1 to 5 carbon atoms, or at least part of at least one member selected from the group consisting of product C comprised mainly of a non-aromatic hydrocarbon product having 4 to 5 carbon atoms and product D comprised mainly of hydrogen and a non-aromatic hydrocarbon product having 1 to 3 carbon atoms (which products B, C and D are obtained by purification and separation of the desired aromatic hydrocarbon product), can be supplied to a high temperature-thermal cracking system of a petroleum hydrocarbon for producing ethylene. In this case, various useful products, such as ethylene, propylene, a $C_4$ fraction, a $C_5$ fraction and an aromatic hydrocarbon product (e.g., benzene, toluene, xylene and the like), can be produced by the above-mentioned high temperature-thermal cracking system of a petroleum hydrocarbon for the production of ethylene.

In the method of the present invention, product A comprised mainly of an aromatic hydrocarbon product can be processed by at least one method selected from the group consisting of the following methods:

a method in which the product A is processed using a dealkylation apparatus to thereby produce benzene;

a method in which the product A is processed using a distillation apparatus, an extraction apparatus or an extractive distillation apparatus to thereby produce benzene, toluene and xylene (hereinafter, those three compounds are collectively referred to as "BTX");

a method in which the product A is processed using a disproportionation apparatus or an isomerization apparatus; and a method in which the product A is blended with gasoline.

The term "dealkylation apparatus" used herein is intended to mean a reactor which is used in a catalytic dealkylation method or a thermal dealkylation method as described at pages 145 to 155 of "Shin Sekiyu Kagaku Purosesu (New Petrochemical Process)" (published by Saiwai Shobo, Japan in 1986), edited by The Japan Petroleum Institute. The term "distillation apparatus" used herein is intended to mean an apparatus which is used in a distillation system as described at pages 183 to 206 of "Purosesu Sekkei Shiriidzu 3, Bunkai.Kanetsu.Joryu Wo Chushin Ni Suru Sekkei (Design of Processes, Series 3, "Designing a system using cracking, heating and distillation as important measures)" (published by Maruzen Co., Ltd., Japan in 1974), edited by The Society of Chemical Engineers Japan. The term "disproportionation apparatus" used herein is intended to mean an apparatus which is used in a disproportionation reaction as described at pages 100 to 115 of "Shin Sekiyu Kagaku Purosesu (New Petrochemical Process)" (published by Saiwai Shobo, Japan in 1986), edited by The Japan Petroleum Institute. The term "isomerization apparatus" used herein is intended to mean an apparatus which is used in an isomerization reaction as described at pages 69 to 88 of "Shin Sekiyu Kagaku Purosesu (New Petrochemical Process)" (published by Saiwai Shobo, Japan in 1986), edited by The Japan Petroleum Institute. The terms "extraction apparatus" and "extractive distillation apparatus" used herein are intended to mean those which are used in an extraction method, a method for extractive distillation or a method for azeotropic distillation as described at pages 206 to 213 of "Purosesu Sekkei Shiriidzu 3, Bunkai.Kanetsu.Joryu Wo Chushin Ni Suru Sekkei (Design of Processes, Series 3, Designing a system using cracking, heating and distillation as important measures)" (published by Maruzen Co., Ltd., Japan in 1974), edited by The Society of Chemical Engineers Japan.

In the method of the present invention, the occurrence of a carbonaceous material (coke) on the zeolite catalyst during the catalytic cyclization reaction can be remarkably decreased. However, if coking occurs on the zeolite catalyst, the supply of the light hydrocarbon feedstock to the fixed-bed, adiabatic reactor can be temporarily stopped, and the coke formed on the zeolite catalyst during the catalytic cyclization reaction can be burnt off with an oxygen-containing inert gas as a burning gas to regenerate the zeolite catalyst in a catalyst regeneration zone. The exhausted burning gas flowing out of the catalyst regeneration zone can be released into the atmosphere or can be recycled to the catalyst regeneration zone by means of a recycling compressor in a manner as described below. In either case, it is preferred to decrease the water content of the oxygen-containing inert gas flowing into the catalyst regeneration zone by contacting the oxygen-containing inert gas with a water adsorbing agent. A representative example of the oxygen-containing inert gas is air.

When the exhausted burning gas flowing out of the catalyst regeneration zone is recycled, it is preferred that the exhausted burning gas be recycled to the catalyst regeneration zone through a heater by means of a recycling compressor to thereby form a burning gas circulation system comprising the catalyst regeneration zone, the recycling compressor and the heater which are connected in this order through a pipeline. In this case, a fresh, oxygen-containing inert gas can be supplied to the burning gas circulation system at a first port positioned between an outlet of the catalyst regeneration zone and an inlet of the heater in an amount of 0.05 to 50% by volume, preferably 2.5 to 10% by volume, based on the circulation volume of the burning gas, while discharging from the burning gas circulation system the exhausted burning gas flowing out of the catalyst regeneration zone before reaching the heater in an amount which is substantially equal to the amount of the fresh, oxygen-containing inert gas supplied to the first port. With respect to the above-mentioned fresh, oxygen-containing inert gas supplied, the amount and oxygen content thereof are adjusted, so that the burning gas flowing into the catalyst regeneration zone has an oxygen content of 0.01 to 10% by volume, preferably 0.5 to 2% by volume. Further, a fresh inert gas containing no oxygen can be supplied to the burning gas circulation system at a second port, which is identical with the first port or is provided separately from the first port between the outlet of the catalyst regeneration zone and the inlet of the heater, in an amount of 10% by volume or less, preferably 5% by volume or less, based on the circulation volume of the burning gas, while incrementally discharging from the burning gas circulation system the exhausted burning gas flowing out of the catalyst regeneration zone before reaching the heater in an amount which is substantially equal to the amount of the fresh inert gas, containing no oxygen, supplied to the second port. This operation can suppress an increase in the partial pressure of steam in the burning gas flowing into the catalyst regeneration zone. As mentioned above, when a fresh inert gas containing no oxygen is supplied to the burning gas circulation system in addition to the fresh, oxygen-containing inert gas, the fresh, oxygen-containing inert gas and the fresh inert gas containing no oxygen may be separately supplied to the burning gas circulation system at a first port and a second port, respectively. On the other hand, the fresh, oxygen-containing inert gas and the fresh inert gas containing no oxygen may be first mixed and then, supplied to the burning gas circulation system at a single port.

Figure 7:
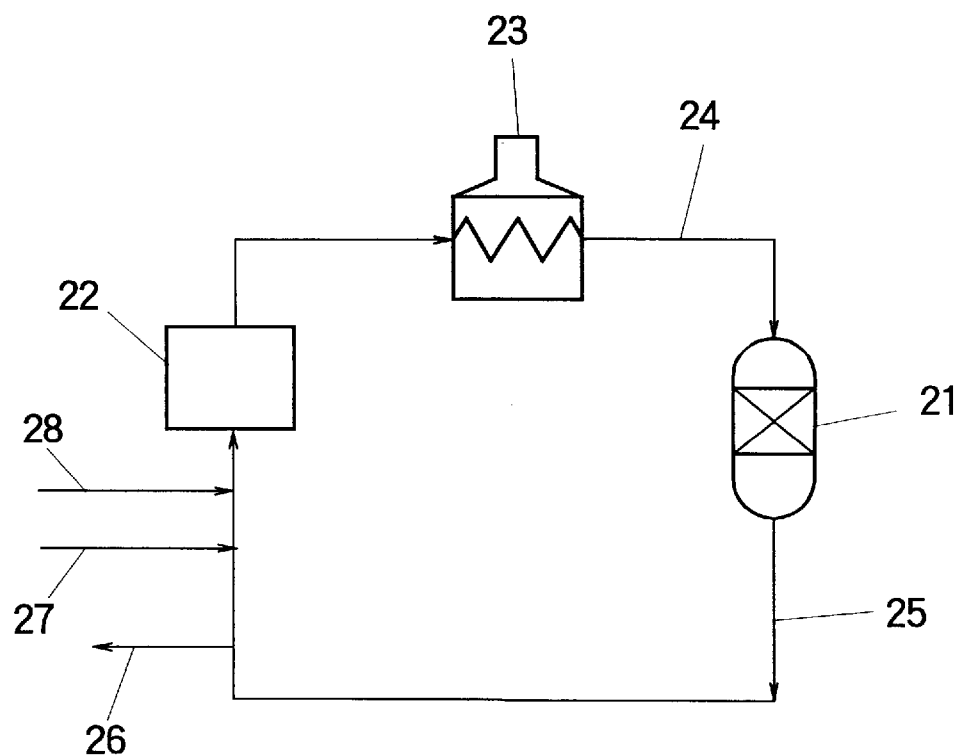
FIG. 7 is a flow sheet showing one mode of the regeneration of the zeolite catalyst used in the method of the present invention.

FIG. 7 is a flow sheet showing one mode of the regeneration of a zeolite catalyst used in the method of the present invention. In the burning gas circulation system shown in FIG. 7, fresh, oxygen-containing inert gas 28 and fresh inert gas 27 containing no oxygen are supplied to the burning gas circulation system at a first port and a second port, respectively. In FIG. 7, fresh, oxygen-containing inert gas 28 (e.g., air), which has been heated to 350° to 600° C., preferably 390° to 580° C., more preferably 420° to 480° C. by means of heater 23, is supplied to the burning gas circulation system in an amount of 0.05 to 50% by volume, preferably 2.5 to 10% by volume, based on the circulation volume of the burning gas so that the oxygen content of burning gas 24 flowing into catalyst regeneration zone 21 containing a zeolite catalyst having coke adhered thereto becomes 0.01 to 10% by volume, preferably 0.5 to 2% by volume. The burning gas comprised of supplied fresh, oxygen-containing inert gas 28 and exhausted burning gas 25 flowing out of catalyst regeneration zone 21 is fed to heater 23 by means of recycling compressor 22. Further, before the burning gas to be compressed reaches recycling compressor 22, or before the compressed burning gas from recycling compressor 22 reaches heater 23 (the latter case not shown), fresh inert gas 27 containing no oxygen is supplied to the burning gas circulation system in an amount of 10% by volume or less, preferably 5% by volume or less, based on the circulation volume of the burning gas. In addition, before the burning gas to be compressed reaches recycling compressor 22, or before the compressed burning gas from recycling compressor 22 reaches heater 23 (the latter case not shown), a part of exhausted burning gas 25 flowing out of catalyst regeneration zone 21 (which part of exhausted burning gas 25 flowing out of catalyst regeneration zone 21 is indicated by numeral 26) is discharged from the burning gas circulation system in an amount which is substantially equal to the total amount of fresh, oxygen-containing inert gas 28 supplied and fresh inert gas 27 containing no oxygen supplied, specifically, for example, in an amount of 0.05 to 60% by volume, preferably 0.05 to 20% by volume, based on the circulation volume of the burning gas, so that the internal pressure of the burning gas circulation system can be maintained at a predetermined level. The port for discharging a part of the exhausted burning gas may be provided at a position downstream of the first port for supplying the fresh, oxygen-containing inert gas and the second port for supplying the fresh inert gas containing no oxygen (this embodiment not shown). By the above operations, it is possible to suppress an increase in the partial pressure of steam in the burning gas flowing into catalyst regeneration zone 21 to thereby largely suppress a lowering of the catalytic activity.

It is preferred that the water content of the burning gas from recycling compressor 22 be lowered before it is supplied to heater 23, by contacting the burning gas with a water adsorbing agent. The inert gas is selected from gases other than those (e.g., alcohol and ether) which generate $H_2O$ upon being contacted with a zeolite. Especially desirable as an inert gas is nitrogen.

In the present invention, the adiabatic reactor may be used not only for a catalytic cyclization reaction but also as a regeneration reactor in the burning gas circulation system for regenerating the zeolite catalyst. In this case, the catalytic cyclization reaction system and the burning gas circulation system commonly use a single reactor which functions as an adiabatic reactor for the catalytic cyclization in the former and also functions as a catalyst regeneration reactor in the latter. That is, after the catalytic cyclization reaction, the adiabatic reactor is used as the regeneration reactor by manipulating appropriate valves so that the adiabatic reactor is disconnected from the system for the catalytic cyclization reaction and connected to and incorporated in the burning gas circulation system for regenerating the zeolite catalyst to form a closed circulation system as shown in FIG. 7. (When two reactors are employed as in the case of the reactor of the double-reactor column type mentioned above or, similarly, three or more reactors are employed, appropriate valves are provided so that at least one catalytic cyclization reaction system and at least one burning gas circulation system, which systems involve a plurality of reactors, can be suitably formed by switching the valves.) Alternatively, the zeolite catalyst used in the catalytic cyclization reaction may be taken out from the adiabatic reactor and transferred to a catalyst regeneration zone in the burning gas circulation system shown in FIG. 7 (which catalyst regeneration zone is provided separately from the adiabatic reactor for the catalytic cyclization reaction) and then, regeneration of the zeolite catalyst may be conducted. Likewise, the heater used for heating the feedstock stream for the catalytic cyclization reaction can also be used as the heater in the burning gas circulation system for regenerating the zeolite catalyst.

Further, the burning gas to be compressed by means of recycling compressor 22 may be cooled, and the compressed burning gas may be heated before reaching heater 23, wherein the cooling and heating can be conducted by means of at least one heat exchanger. The above-mentioned cooling of the burning gas to be compressed by means of recycling compressor 22 is intended to increase the efficiency of recycling compressor 22, and the above-mentioned heating of the compressed burning gas before reaching heater 23 is intended to lower the burden on heater 23. The heat exchange can be effected by either of the following two methods. That is, in one method, a section of pipeline connecting the outlet of the catalyst regeneration zone to the inlet of the recycling compressor and a section of pipeline connecting the outlet of the recycling compressor to the inlet of the heater are arranged so that both of the sections pass through a single heat exchanger (not shown) and the cooling and heating are effected by the single heat exchanger. Alternatively, in the other method, a section of pipeline connecting the outlet of the catalyst regeneration zone to the inlet of the recycling compressor and a section of pipeline connecting the outlet of the recycling compressor to the inlet of the heater are, respectively, provided with a heat exchanger for cooling (not shown) and a heat exchanger for heating (not shown), so that the cooling and heating are effected by means of two separate heat exchangers, respectively.

In the method of the present invention, the steaming of the substantially fresh zeolite catalyst can be performed using a steam circulation system including a steaming reactor, a recycling compressor, a heater and at least one heat exchanger, which are connected through a pipeline. In this case, it is preferred that the steaming reactor be used as the adiabatic reactor for the catalytic cyclization reaction. Further, it is preferred that the steam circulation system be utilized as the above-mentioned burning gas circulation system for the regeneration of the zeolite catalyst. In this case, the steaming reactor is used as or replaced by a regeneration reactor comprising the catalyst regeneration zone in the burning gas circulation system, and the burning gas for the burning gas circulation system is used in place of the steam for the steam circulation system. In the present invention, it is preferred that the steaming reactor be used also as the adiabatic reactor and as the regeneration reactor.

The term "recycling compressor" used herein is intended to mean the displacement compressor, displacement blower, centrifugal compressor, centrifugal blower, axial compressor, axial blower and the like, which are described at pages 11 to 46 of "Dai 10 Pen Kuuki Kikai (Section 10 Pneumatic machinery)" of "Kikai Kogaku Handobukku, Kaitei Dai 6 Pan (Handbook of Mechanical Engineering, 6th revised edition)" (published by The Japan Society of Mechanical Engineering in 1977) edited by The Japan Society of Mechanical Engineering.

BEST MODE FOR CARRYING OUT THE INVENTION

The present invention will now be further illustrated in more detail with reference to the following Examples and Comparative Examples, which should not be construed as limiting the scope of the present invention.

EXAMPLE 1

60 parts by w eight of ZSM-5 crystalline alumino-silicate (having an Si/Al atomic ratio of 46 in a zeolite structure thereof) in ammonium ion form, 15 parts by weight of γ-alumina and 25 parts by weight of zinc nitrate were kneaded, and the resultant mixture was subjected to extrusion molding, thereby obtaining a molded product having a diameter of 1.6 mm and a length of 4 to 6 mm. The molded product was dried at 120° C. for 4 hours and, then, calcined at 500° C. for 3 hours to obtain a molded ZSM-5 zeolite catalyst having a zinc content of 10% by weight.

Then, a fixed-bed, single-stage, adiabatic reactor was packed with the obtained molded zeolite catalyst to form a catalyst bed. A steam-nitrogen gas mixture containing 40% by volume of steam and having a pressure of 1 kg/cm$^2$·G and a temperature of 650° C., was fed to and flowed through the reactor for 5 hours to effect a steaming of the zeolite catalyst.

For evaluating the initial-stage catalytic activity of the molded zeolite catalyst thus-steamed, the conversion reaction test for n-hexane was conducted using a sample of the zeolite catalyst under isothermal conditions, in an isothermal reactor shown in FIG. 8. Illustratively stated, according to the above-mentioned method, a decomposition reaction of n-hexane was conducted in the reactor at 500° C. under atmospheric pressure, and at a weight hourly space velocity (WHSV) of 4 hr$^{-1}$ with respect to the n-hexane. As a result, it was found that the average initial stage, first-order reaction rate constant of the decomposition of n-hexane catalyzed by the zeolite-catalyst for the gas-oil collection time of 0.25 hour was 0.28 (sec$^{-1}$).

Then, a feedstock was prepared by mixing a $C_5$ fraction indicated in Table 2 with a $C_4$ fraction indicated in Table 1 in a weight ratio of 3:7 so that the resultant feedstock had a weight ratio of unsaturated hydrocarbons/saturated hydrocarbons of 1.54, which is within the range of from 0.43 to 2.33. The obtained feedstock was heated to 530° C. and fed to and flowed through the fixed-bed, single stage, adiabatic reactor, to thereby effect a catalytic cyclization reaction. Results of the reaction, as obtained 10 hours and 5 days after the start of the reaction, are shown in Table 3, together with the reaction conditions.

Comparative Example 1

Substantially the same procedure as in Example 1 was repeated, except that a feedstock composed only of a $C_5$ fraction (weight ratio of unsaturated hydrocarbons/saturated hydrocarbons: 0.37) indicated in Table 2 was used. Results of the reaction, as obtained 10 hours and 5 days after the start of the reaction, are shown in Table 3, together with the reaction conditions.

27

Comparative Example 2

Substantially the same procedure as in Example 1 was repeated, except that a feedstock composed only of a $C_4$ fraction (weight ratio of unsaturated hydrocarbons/saturated hydrocarbons: 3.00) indicated in Table 1 was used. Results of the reaction, as obtained 10 hours and 5 days after the start of the reaction, are shown in Table 3, together with the reaction conditions.

The results of Comparative Examples 1 and 2 shown in Table 3 show that when the reaction conditions do not satisfy all of the requirements (1), (2), (3) and (4) defined in the present invention, there would occur problems such that the yield of aromatic hydrocarbons is lowered and a stable reaction cannot be conducted.

EXAMPLE 2

Substantially the same procedure as in Comparative Example 2 was repeated, except that the internal pressure of the fixed-bed, single-stage, adiabatic reactor was 1 kg/cm$^2$·G. Results of the reaction, as obtained 10 hours and 3 days after the start of the reaction, are shown in Table 4, together with the reaction conditions. Results of the reaction in Comparative Example 2, as obtained 10 hours and 3 days after the start of the reaction, are also shown in Table 4.

EXAMPLE 3

A $C_4$ fraction (weight ratio of unsaturated hydrocarbons/saturated hydrocarbons: 3.00) indicated in Table 1 was heated to 530° C. and fed to a fixed-bed, single-stage, adiabatic reactor packed with a catalyst bed of a zeolite catalyst which was obtained by the same method as in Example 1. The obtained reaction product was separated into product A comprised mainly of an aromatic hydrocarbon product, product C comprised mainly of a non-aromatic hydrocarbon product having 4 to 5 carbon atoms and product D comprised mainly of hydrogen and a non-aromatic hydrocarbon product having 1 to 3 carbon atoms. The separation was performed by means of a gas-liquid separator and a distillation column. Then, product C was recycled to the fixed-bed, single-stage, adiabatic reactor. The reaction conditions satisfied all of the requirements (1), (2), (3) and (4) defined in the present invention. Results of the reaction, as obtained 10 hours and 3 days after the start of the reaction, are shown in Table 4, together with the reaction conditions.

Table 4 shows that when the reaction conditions satisfy all of the requirements (1), (2), (3) and (4) defined in the present invention, aromatic hydrocarbons can be obtained in high yield and a stable reaction can be conducted, irrespective of the composition of the feedstock.

Comparative Example 3

60 parts by Weight of ZSM-5 crystalline alumino-silicate (having an Si/Al atomic ratio of 46 in a zeolite structure thereof) in ammonium ion form, 15 parts by weight of γ-alumina and 25 parts by weight of zinc nitrate were kneaded, and the resultant mixture was subjected to extrusion molding, thereby obtaining a molded product having a diameter of 1.6 mm and a length of 4 to 6 mm. The molded product was dried at 120° C. for 4 hours and, then, calcined at 500° C. for 3 hours to obtain a molded ZSM-5 zeolite catalyst having a zinc content of 10% by weight.

Then, a fixed-bed, single-stage, adiabatic reactor was packed with the obtained molded zeolite catalyst to form a catalyst bed. A steam-nitrogen gas mixture containing 40% by volume of steam and having a pressure of 1 kg/cm$^2$·G and a temperature of 650° C., was fed to and flowed through the reactor for 1 hour to effect a steaming of the zeolite catalyst.

For evaluating the initial-stage catalytic activity of the molded zeolite catalyst thus steamed, the conversion reaction test for n-hexane was conducted using a sample of the zeolite catalyst under isothermal conditions in the same manner as in Example 1. As a result, it was found that the initial stage, first-order reaction rate constant of the decomposition of n-hexane catalyzed by the zeolite catalyst was 0.55 (sec$^{-1}$).

Then, a $C_5$ fraction (weight ratio of unsaturated hydrocarbons/saturated hydrocarbons: 0.37, which is outside the range of from 0.43 to 2.33) indicated in Table 2 was heated to 530° C. and fed to the fixed-bed, single-stage, adiabatic reactor. Results of the reaction, as obtained 10 hours after the start of the reaction, are shown in Table 5, together with the reaction conditions.

Comparative Example 4

Substantially the same procedure as in Comparative Example 3 was repeated, except that a $C_4$ fraction weight ratio of unsaturated hydrocarbons/saturated hydrocarbons: 3.00) indicated in Table 1 was used. Results of the reaction, as obtained 10 hours after the start of the reaction, are shown in Table 5, together with the reaction conditions.

Example 4

Substantially the same procedure as in Comparative Example 3 was repeated, except that a feedstock (weight ratio of unsaturated hydrocarbons/saturated hydrocarbons: 1.54) which was prepared by mixing a $C_5$ fraction indicated in Table 2 with a $C_4$ fraction indicated in Table 1 in a weight ratio of 3:7, was used. Results of the reaction, as obtained 10 hours after the start of the reaction, are shown in Table 5, together with the reaction conditions.

Table 5 shows that, under the above-mentioned conditions, the yield of aromatic hydrocarbons (56.7% by weight) obtained in Example 4 by reacting a feed-stock which was prepared by mixing a $C_5$ fraction with a $C_4$ fraction in a weight ratio of 3:7 is higher than the yield of aromatic hydrocarbons (54.7% by weight) (hereinafter referred to as calculated yield of aromatic hydrocarbons) in a reaction product mixture obtained by mixing a reaction product from the reaction of a feedstock composed only of a $C_5$ fraction (Comparative Example 3) with a reaction product from the reaction of a feedstock composed only of a $C_4$ fraction (Comparative Example 4) in a weight ratio of 3:7. The above-mentioned calculated yield of aromatic hydrocarbons is obtained by the following formula: (the yield of aromatic hydrocarbons obtained in Comparative Example 3)×0.3+(the yield of aromatic hydrocarbons obtained in Comparative Example 4)×0.7.

With respect to each of Comparative Examples 3 and 4, and Example 4, the yield of aromatic hydrocarbons which was obtained 5 days after the start of the reaction is shown in Table 5. The results show that, under the reaction conditions in Example 4, aromatic hydrocarbons can be obtained in high yield and a stable reaction can be conducted.

Comparative Example 5

A fixed-bed, single-stage, adiabatic reactor was packed with the molded ZSM-5 zeolite catalyst obtained by the same method as in Comparative Example 3 to form a catalyst bed. A steam-nitrogen gas mixture containing 40% by volume of steam and having a pressure of 1 kg/cm$^2$·G and a temperature of 650° C., was fed to and flowed through the fixed-bed, single-stage, adiabatic reactor for 5 hours to effect a steaming of the zeolite catalyst.

For evaluating the initial-stage catalytic activity of the molded zeolite catalyst thus steamed, the conversion reaction test for n-hexane was conducted using a sample of the zeolite catalyst under isothermal conditions in the same manner as in Example 1. As a result, it was found that the initial stage, first-order reaction rate constant of the decomposition of n-hexane catalyzed by the zeolite catalyst was 0.28 (sec$^{-1}$).

Then, a $C_5$ fraction (weight ratio of unsaturated hydrocarbons/saturated hydrocarbons: 0.37, which is outside the range of from 0.43 to 1.33) indicated in Table 2 was heated to 500° C. and fed to the fixed-bed, single-stage, adiabatic reactor. Results of the reaction, as obtained 10 hours after the start of the reaction, are shown in Table 5, together with the reaction conditions.

Comparative Example 6

Substantially the same procedure as in Comparative Example 5 was repeated, except that a $C_4$ fraction (weight ratio of unsaturated hydrocarbons/saturated hydrocarbons: 3.00) indicated in Table 1 was used. Results of the reaction, as obtained 10 hours after the start of the reaction, are shown in Table 5, together with the reaction conditions.

Example 5

Substantially the same procedure as in Comparative Example 5 was repeated, except that a feedstock (weight ratio of unsaturated hydrocarbons/saturated hydrocarbons: 1.54) which was prepared by mixing a $C_5$ fraction indicated in Table 2 with a $C_4$ fraction indicated in Table 1 in a weight ratio of 3:7, was used. Results of the reaction, as obtained 10 hours after the start of the reaction, are shown in Table 5, together with the reaction conditions.

As shown in Table 5, the yield of aromatic hydrocarbons obtained in Example 5 (51.2% by weight) is higher than the calculated yield of aromatic hydrocarbons (49.3% by weight) calculated from the yields of aromatic hydrocarbons obtained in Comparative Examples 5 and 6.

Comparative Example 7

A molded ZSM-5 zeolite catalyst obtained by the same method as in comparative Example 3 was steamed under the same conditions as in Comparative Example 5.

For evaluating the initial-stage catalytic activity of the molded zeolite catalyst thus steamed, the conversion reaction test for n-hexane was conducted using a sample of the zeolite catalyst under isothermal conditions in the same manner as in Example 1. As a result, it was found that the initial stage, first-order reaction rate constant of the decomposition of n-hexane catalyzed by the zeolite catalyst was 0.28 (sec$^{-1}$).

Then, a $C_5$ fraction (weight ratio of unsaturated hydrocarbons/saturated hydrocarbons: 0.37) indicated in Table 2 was heated to 450° C. and fed to the fixed-bed, single-stage, adiabatic reactor. Results of the reaction, as obtained 10 hours after the start of the reaction, are shown in Table 5, together with the reaction conditions.

Comparative Example 8

Substantially the same procedure as in Comparative Example 7 was repeated, except that a $C_4$ fraction (weight ratio of unsaturated hydrocarbons/saturated hydrocarbons: 3.00) indicated in Table 1 was used. Results of the reaction, as obtained 10 hours after the start of the reaction, are shown in Table 5, together with the reaction conditions.

Comparative Example 9

A molded ZSM-5 zeolite catalyst obtained by the same method as in comparative Example 3 was steamed under the same conditions as in Comparative Example 5.

Then, a feedstock was prepared by mixing a $C_5$ fraction indicated in Table 2 with a $C_4$ fraction indicated in Table 1 in a weight ratio of 3:7 so, that the resultant feedstock had a weight ratio of unsaturated hydrocarbons/saturated hydrocarbons of 1.54, which is within the range of from 0.43 to 2.33. The obtained feedstock was heated to 450° C. and fed to the fixed-bed, single-stage, adiabatic reactor. Results of the reaction, as obtained 10 hours after the start of the reaction, are shown in Table 5, together with the reaction conditions.

As shown in Table 5, the yield of aromatic hydrocarbons (43.9% by weight) obtained in Comparative Example 9 by reacting a feedstock which was prepared by mixing a $C_5$ fraction with a $C_4$ fraction in a weight ratio of 3:7 is lower than the calculated yield of aromatic hydrocarbons (44.7% by weight) calculated from the yields of aromatic hydrocarbons obtained in Comparative Examples 7 and 8.

EXAMPLE 6

60 parts by weight of ZSM-5 crystalline alumino-silicate (having an Si/Al atomic ratio of 46 in a zeolite structure thereof) in ammonium ion form, 15 parts by weight of γ-alumina and 25 parts by weight of zinc nitrate were kneaded, and the resultant mixture was subjected to extrusion molding, thereby obtaining a molded product having a diameter of 1.6 mm and a length of 4 to 6 mm. The molded product was dried at 120° C. for 4 hours and, then, calcined at 500° C. for 3 hours to obtain a molded ZSM-5 zeolite catalyst having a zinc content of 10% by weight.

Then, a fixed-bed, single-stage, adiabatic reactor was packed with the obtained molded zeolite catalyst to form a catalyst bed. A steam-nitrogen gas mixture containing 40% by volume of steam and having a pressure of 1 kg/cm$^2$·G and a temperature of 650° C., was fed to and flowed through the fixed-bed, single-stage, adiabatic reactor for 5 hours to effect a steaming of the zeolite catalyst.

For evaluating the initial-stage catalytic activity of the molded zeolite catalyst thus steamed, the conversion reaction test for n-hexane was conducted using a sample of the zeolite catalyst under isothermal conditions in the same manner as in Example 1. As a result, it was found that the initial stage, first-order reaction rate constant of the decomposition of n-hexane catalyzed by the zeolite catalyst was 0.28 (sec$^{-1}$).

Then, a feedstock was prepared by mixing a $C_5$ fraction indicated in Table 2 with a $C_4$ fraction indicated in Table 1 in a weight ratio of 6:4. The obtained feedstock (weight ratio of unsaturated hydrocarbons/saturated hydrocarbons: 0.86) was heated to 530° C. and fed to the fixed-bed, single-stage, adiabatic reactor. Results of the reaction, as obtained 10 hours after the start of the reaction, are shown in Table 6, together with the reaction conditions.

Comparative Example 10

Substantially the same procedure as in Example 6 was repeated, except that a molded ZSM-5 zeolite catalyst was steamed for 40 hours so that the initial-stage catalytic activity thereof became less than 0.2 (sec$^{-1}$). Results of the reaction, as obtained 10 hours after the start of the reaction, are shown in Table 6, together with the reaction conditions.

EXAMPLE 7

46.4 parts by weight of ZSM-5 crystalline alumino-silicate (having an Si/Al atomic ratio of 46 in a zeolite structure thereof) in ammonium ion form, 11.6 parts by weight of γ-alumina and 42 parts by weight of zinc aluminate were kneaded, and the resultant mixture was subjected to extrusion molding, thereby obtaining a molded product having a diameter of 1.6 mm and a length of 4 to 6 mm. The molded product was dried at 120° C. for 4 hours and then, calcined at 500° C. for 3 hours to obtain a molded ZSM-5 zeolite catalyst having a zinc content of 20% by weight.

Then, a fixed-bed, single-stage, adiabatic reactor was packed with the obtained molded zeolite catalyst to form a catalyst bed. A steam-nitrogen gas mixture containing 40% by volume of steam and having a pressure of 1 kg/cm$^2$·G and a temperature of 650° C., was fed to and flowed through the fixed-bed, single-stage, adiabatic reactor for 5 hours to effect a steaming of the zeolite catalyst.

Then, a feedstock was prepared by mixing a $C_5$ fraction indicated in Table 2 with a $C_4$ fraction indicated in Table 1 in a weight ratio of 6:4. The obtained feedstock (weight ratio of unsaturated hydrocarbons/saturated hydrocarbons: 0.86) was heated to 530° C. and fed to the fixed-bed, single-stage, adiabatic reactor. Results of the reaction, as obtained 10 hours after the start of the reaction, are shown in Table 6, together with the reaction conditions.

Comparative Example 11

ZSM-5 crystalline alumino-silicate (having an Si/Al atomic ratio of 46 in a zeolite structure thereof) in sodium ion form was subjected to ion exchange so that the sodium content of the zeolite became 3000 wt ppm, thereby obtaining ZSM-5 crystalline alumino-silicate in ammonium ion form. 60 parts by weight of the above-mentioned ZSM-5 crystalline alumino-silicate in ammonium ion form, 15 parts by weight of γ-alumina and 25 parts by weight of zinc nitrate were kneaded, and the resultant mixture was subjected to extrusion molding, thereby obtaining a molded product having a diameter of 1.6 mm and a length of 4 to 6 mm. The molded product was dried at 120° C. for 4 hours and then, calcined at 500° C. for 3 hours to obtain a molded ZSM-5 zeolite catalyst having a zinc content of 10% by weight.

In this experiment, the measurement of the sodium content of the zeolite catalyst was conducted by a method in which the catalyst is added to an aqueous 1N-HCl solution and the resultant mixture is heated for 5 minutes and subjected to filtration to obtain a filtrate, and the filtrate is analyzed by means of an atomic absorption spectrometer (AA-640-12, manufactured and sold by Shimadzu Corporation, Japan).

Then, a fixed-bed, single-stage, adiabatic reactor was packed with the obtained molded zeolite catalyst to form a catalyst bed. A steam-nitrogen gas mixture containing 40% by volume of steam and having a pressure of 1 kg/cm$^2$·G and a temperature of 650° C., was fed to and flowed through the fixed-bed, single-stage, adiabatic reactor for 5 hours to effect a steaming of the zeolite catalyst.

For evaluating the initial-stage catalytic activity of the molded zeolite catalyst thus steamed, the conversion reaction test for n-hexane was conducted using a sample of the zeolite catalyst under isothermal conditions in the same manner as in Example 1. As a result, it was found that the initial stage, first-order reaction rate constant of the decomposition of n-hexane catalyzed by the zeolite catalyst was 0.05 (sec$^{-1}$)

Then, a feedstock was prepared by mixing a $C_5$ fraction indicated in Table 2 with a $C_4$ fraction indicated in Table 1 in a weight ratio of 6:4. The obtained feedstock (weight ratio of unsaturated hydrocarbons/saturated hydrocarbons: 0.86) was heated to 530° C. and fed to the fixed-bed, single-stage, adiabatic reactor. Results of the reaction, as obtained 10 hours after the start of the reaction, are shown in Table 7, together with the reaction conditions.

The sodium content of the zeolite catalyst which was used in Example 6 was measured by the same method as described above. As a result, it was found that its sodium content was 110 wt ppm. For comparison, the conditions and results of Example 6, including the sodium content of the zeolite catalyst, are also shown in Table 7.

EXAMPLE 8

Substantially the same procedure as in Example 6 was repeated, except that a reaction product obtained by the catalytic cyclization reaction was separated into product A comprised mainly of an aromatic hydrocarbon product, product C comprised mainly of a non-aromatic hydrocarbon product having 4 to 5 carbon atoms and product D comprised mainly of hydrogen and a non-aromatic hydrocarbon product having 1 to 3 carbon atoms by means of a gas-liquid separator and a distillation column, and product C was recycled to the fixed-bed, single-stage, adiabatic reactor.

Illustratively stated, 60 parts by weight of ZSM-5 crystalline alumino-silicate (having an Si/Al atomic ratio of 46 in a zeolite structure thereof) in ammonium ion form, 15 parts by weight of γ-alumina and 25 parts by weight of zinc nitrate were kneaded, and the resultant mixture was subjected to extrusion molding, thereby obtaining a molded product having a diameter of 1.6 mm and a length of 4 to 6 mm. The molded product was dried at 120° C. for 4 hours and then, calcined at 500° C. for 3 hours to obtain a molded ZSM-5 zeolite catalyst having a zinc content of 10% by weight.

Then, a fixed-bed, single-stage, adiabatic reactor was packed with the obtained molded zeolite catalyst to form a catalyst bed. A steam-nitrogen gas mixture containing 40% by volume of steam and having a pressure of 1 kg/cm$^2$·G and a temperature of 650° C., was fed to and flowed through the fixed-bed, single-stage, adiabatic reactor for 5 hours to effect a steaming of the zeolite catalyst.

For evaluating the initial-stage catalytic activity of the molded zeolite catalyst thus steamed, the conversion reaction test for n-hexane was conducted using a sample of the zeolite catalyst under isothermal conditions in the same manner as in Example 1. As a result, it was found that the initial stage, first-order reaction rate constant of the decomposition of n-hexane catalyzed by the zeolite catalyst was 0.28 (sec$^{-1}$).

Then, a feedstock was prepared by mixing a $C_5$ fraction indicated in Table 2 with a $C_4$ fraction indicated in Table 1 in a weight ratio of 6:4. The obtained feedstock (weight ratio of unsaturated hydrocarbons/saturated hydrocarbons: 0.86) was heated to 530° C. and fed to the fixed-bed, single-stage, adiabatic reactor. The resultant reaction product was separated into product A comprised mainly of an aromatic hydrocarbon product, product C comprised mainly of a non-aromatic hydrocarbon product having 4 to 5 carbon atoms and product D comprised mainly of hydrogen and a non-aromatic hydrocarbon product having 1 to 3 carbon atoms. The separation was performed by means of a gas-liquid separator and a distillation column. In the separation of the reaction product into products A, C and D, use was made of a coolant comprised of propylene which was produced in and used as a coolant in a process for producing ethylene. Then, product C was recycled to the fixed-bed, single-stage, adiabatic reactor. Results of the reaction, as obtained 10 hours after the start of the reaction, are shown in Table 8, together with the reaction conditions. As shown in Table 8, the yield of $C_6$–$C_9$ aromatic hydrocarbons obtained in Example 8 is higher than that of $C_6$–$C_9$ aromatic hydrocarbons obtained in Example 6.

EXAMPLE 9

Substantially the same procedure as in Example 8 was repeated, except that the obtained product C comprised mainly of a non-aromatic hydrocarbon product having 4 to 5 carbon atoms was not recycled to the fixed-bed, single-stage, adiabatic reactor, but was fed to a thermal-cracking apparatus to thereby effect a thermal cracking of product C.

Illustratively stated, a molded ZSM-5 zeolite catalyst obtained by the same method as in Example 8 was steamed under the same conditions as in Example 8.

Then, a feedstock was prepared by mixing a $C_5$ fraction indicated in Table 2 with a $C_4$ fraction indicated in Table 1 in a weight ratio of 6:4. The obtained feedstock (weight ratio of unsaturated hydrocarbons/saturated hydrocarbons: 0.86) was heated to 530° C. and fed to the fixed-bed, single-stage, adiabatic reactor. The resultant reaction product was separated into product A comprised mainly of an aromatic hydrocarbon product, product C comprised mainly of a non-aromatic hydrocarbon product having 4 to 5 carbon atoms and product D comprised mainly of hydrogen and a non-aromatic hydrocarbon product having 1 to 3 carbon atoms. The separation was performed by means of a gas-liquid separator and a distillation column, and in the separation, a coolant comprised of propylene which was produced in and used as a coolant in a process for producing ethylene was used. The obtained product C was subjected to thermal cracking in a thermal-cracking apparatus, under conditions such that the pressure was atmospheric pressure, steam dilution ratio was 0.35, COT (Coil Outlet Temperature) was 825° C. and contact time was 0.32 second. Results are shown in Table 9.

EXAMPLE 10

Substantially the same procedure as in Example 8 was repeated, except that the obtained product C comprised mainly of a non-aromatic hydrocarbon product having 4 to 5 carbon atoms was not recycled to the fixed-bed, single-stage, adiabatic reactor, and that the obtained product A comprised mainly of an aromatic hydrocarbon product, was subjected to dealkylation.

Illustratively stated, a molded ZSM-5 zeolite catalyst obtained by the same method as in Example 8 was steamed under the same conditions as in Example 8.

Then, a feedstock was prepared by mixing a $C_5$ fraction indicated in Table 2 with a $C_4$ fraction indicated in Table 1 in a weight ratio of 6:4. The obtained feedstock (weight ratio of unsaturated hydrocarbons/saturated hydrocarbons: 0.86) was heated to 530° C. and fed to the fixed-bed, single-stage, adiabatic reactor. The resultant reaction product was separated into product A comprised mainly of an aromatic hydrocarbon product, product C comprised mainly of a non-aromatic hydrocarbon product having 4 to 5 carbon atoms and product D comprised mainly of hydrogen and a non-aromatic hydrocarbon product having 1 to 3 carbon atoms. The separation was performed by means of a gas-liquid separator and a distillation column, and in the separation, a coolant comprised of propylene which was produced in and used as a coolant in a process for producing ethylene was used. The obtained product A was subjected to dealkylation under conditions such that the total conversion of aromatic hydrocarbons was 70%. Results are shown in Table 10.

EXAMPLE 11

(i) 60 parts by weight of ZSM-5 crystalline aluminosilicate (having an Si/Al atomic ratio of 46 in a zeolite structure thereof) in ammonium ion form, 15 parts by weight of γ-alumina and 25 parts by weight of zinc nitrate were kneaded, and the resultant mixture was subjected to extrusion molding, thereby obtaining a molded product having a diameter of 1.6 mm and a length of 4 to 6 mm. The molded product was dried at 120° C. for 4 hours and then, calcined at 500° C. for 3 hours to obtain a molded ZSM-5 zeolite catalyst having a zinc content of 10% by weight.

(ii) In practicing the steaming in a first-stage, a fixed-bed, single-stage, adiabatic reactor was packed with the obtained molded zeolite catalyst to form a catalyst bed, and the catalyst bed was heated to 600° C. under flowing nitrogen. A steam-nitrogen gas mixture containing 40% by volume of steam and having a pressure of 1 kg/cm$^2$·G (in which the steam partial pressure is 0.8 kg/cm$^2$) and a temperature of 600° C., was fed to and flowed through the reactor at a weight hourly space velocity (WHSV) of 0.08 hr$^{-1}$ for 10 minutes. With respect to 7 equilength blocks of the catalyst bed which are arranged along the direction of steam flow, changes with time of the temperature of each of the blocks during the steaming were measured. Then, in a second-stage, the feeding and flowing of the steam were, first, temporarily stopped and the steam remaining in the reactor was purged with a nitrogen gas. The temperature of the catalyst bed was elevated to and fixed at 640° C. under flowing nitrogen. Subsequently, a steam-nitrogen gas mixture containing 40% by volume of steam and having a pressure of 1 kg/cm$^2$·G (in which the steam partial pressure is 0.8 kg/cm$^2$) and a temperature of 640° C., was fed to and flowed through the reactor at a WHSV of 0.08 hr$^{-1}$ for 14 minutes. Changes with time of the temperature of each of the blocks during the steaming were measured.

The above steaming was conducted using a recycling compressor, a heat exchanger, a heater and a pipeline, which are to be used for regenerating the catalyst by burning.

(iii) For evaluating the degree of dealumination of the molded zeolite catalyst thus steamed, the conversion reaction test for n-hexane was conducted. It is well known that the initial stage, first-order reaction rate constant of the decomposition of n-hexane catalyzed by the zeolite catalyst is in proportion to the Si/Al atomic ratio of a zeolite in a zeolite catalyst. Accordingly, a portion of each of the 7 equilength blocks of the catalyst bed of the above-obtained partially dealuminated zeolite catalyst was taken out and, with respect to the portion of each of the 7 equilength blocks of the steamed catalyst bed, the initial stage, first-order reaction rate constant of the decomposition of n-hexane was obtained by the same method as in Example 1.

The activity of the zeolite catalyst, and the average temperature of each of the uppermost part and lowermost part of the catalyst bed during the steaming are shown in Table 11, together with the reaction conditions of the partial dealumination of the zeolite catalyst. The initial stage, first-order reaction rate constant of the decomposition of n-hexane catalyzed by the zeolite catalyst shown in Table 11 is in proportion to the degree of dealumination of the zeolite.

In Table 11, the uppermost part of the catalyst bed means the uppermost block of the 7 equilength blocks of the catalyst bed, and the lowermost part of the catalyst bed means the lowermost block of the 7 equilength blocks of the catalyst bed. The average temperature of the uppermost part of the catalyst bed means the average temperature obtained with respect to the upper to lower portions of the uppermost part of the catalyst bed, and the average temperature of the lowermost part of the catalyst bed means the average temperature obtained with respect to the upper to lower portions of the lowermost part of the catalyst bed.

Then, a feedstock was prepared by mixing a $C_5$ fraction indicated in Table 2 with a $C_4$ fraction indicated in Table 1 in a weight ratio of 6:4. The obtained feedstock (weight ratio of unsaturated hydrocarbons/saturated hydrocarbons: 0.86) was heated to 530° C. and fed to the fixed-bed, single-stage, adiabatic reactor. Results of the reaction, as obtained 10 hours after the start of the reaction, are shown in Table 11, together with the reaction conditions.

After the reaction, the uppermost part of the catalyst bed was taken out and, the amount of coke which had been formed on the zeolite catalyst during the reaction was determined by means of CHN CORDER MODEL MT-5 manufactured and sold by Yanaco Co., Ltd., Japan.

EXAMPLE 12

A molded ZSM-5 zeolite catalyst was obtained by the same method as in step (i) of Example 11. In substantially the same manner as in Example 11, steaming of the molded zeolite catalyst was conducted, except that the second-stage operation of step (ii) was not performed. Illustratively stated, a fixed-bed, single-stage, adiabatic reactor was packed with a molded ZSM-5 zeolite catalyst which was obtained by the same method as in step (i) of Example 11 to form a catalyst bed, and the catalyst bed was heated to 600° C. under flowing nitrogen. A steam-nitrogen gas mixture containing 40% by volume of steam and having a pressure of 1 $kg/cm^2 \cdot G$ (in which the steam partial pressure is 0.8 $kg/cm^2$) and a temperature of 600° C., was fed to and flowed through the reactor at a WHSV of 0.08 $hr^{-1}$ for one hour. With respect to 7 equilength blocks of the catalyst bed which are arranged along the direction of steam flow, changes with time of the temperature of each of the blocks during the steaming were measured. The activity of the steamed zeolite catalyst was then evaluated in the same manner as in step (iii) of Example 11. The respective activities of the uppermost part, middle part and lowermost part of the catalyst bed of the partially dealuminated zeolite catalyst, and the average temperature of each of the uppermost part and lowermost part of the catalyst bed during the steaming are shown in Table 11.

Then, a feedstock was prepared by mixing a $C_5$ fraction indicated in Table 2 with a $C_4$ fraction indicated in Table 1 in a weight ratio of 6:4. The obtained feedstock (weight ratio of unsaturated hydrocarbons/saturated hydrocarbons: 0.86) was heated to 530° C. and fed to the fixed-bed, single-stage, adiabatic reactor. Results of the reaction, as obtained 10 hours after the start of the reaction, are shown in Table 11, together with the reaction conditions.

The uppermost part of the catalyst bed was taken out and, the amount of coke which had been formed on the zeolite catalyst during the reaction was determined in the same manner as in Example 11. Results are shown in Table 11 as a relative amount of coke to the amount of coke determined in Example 11.

Table 11 shows that when the steaming of the zeolite catalyst is conducted in 2 stages, occurrence of coking on the zeolite catalyst during the reaction can be effectively suppressed.

EXAMPLE 13

60 parts by weight of ZSM-5 crystalline alumino-silicate (having an Si/Al atomic ratio of 46 in a zeolite structure thereof) in ammonium ion form, 15 parts by weight of γ-alumina and 25 parts by weight of zinc nitrate were kneaded, and the resultant mixture was subjected to extrusion molding, thereby obtaining a molded product having a diameter of 1.6 mm and a length of 4 to 6 mm. The molded product was dried at 120° C. for 4 hours and, then, calcined at 500° C. for 3 hours to obtain a molded ZSM-5 zeolite catalyst having a zinc content of 10% by weight.

Then, a fixed-bed, single-stage, adiabatic reactor was packed with the obtained molded zeolite catalyst to form a catalyst bed. A steam-nitrogen gas mixture containing 40% by volume of steam and having a pressure of 1 $kg/cm^2 \cdot G$ and a temperature of 650° C., was fed to and flowed through the reactor for 5 hours to effect a steaming of the zeolite catalyst.

(i) Then, a feedstock was prepared by mixing a $C_5$ fraction indicated in Table 2 with a $C_4$ fraction indicated in Table 1 in a weight ratio of 6:4. The obtained feedstock (weight ratio of unsaturated hydrocarbons/saturated hydrocarbons: 0.86) was heated to a temperature of from 530° to 550° C. and fed to and flowed through the fixed-bed, single-stage, adiabatic reactor for 2 days.

(ii) Then, the feeding of the feedstock was stopped, and the burning off of coke which had been formed on the zeolite catalyst was conducted for about 2 days under the conditions mentioned below, by means of a burning gas circulation system as shown in FIG. 7, thereby regenerating the catalyst.

| | |
|---|---|
| Circulation volume of burning gas | 5000 $m^3/hr$ (as measured at 0° C. under atmospheric pressure) |
| Oxygen concentration | 0.8 to 1.2% by volume |
| Amount of exhausted burning gas discharged from burning gas circulation system | 7.3 to 9.2% by volume |
| GHSV | 530 $hr^{-1}$ |
| Pressure | 5 $kg/cm^2 \cdot G$ |
| Temperature | 420 to 520° C. |

In the regeneration of the catalyst, gas 27 (a fresh inert gas) indicated in FIG. 7 (hereinafter referred to as a "makeup gas") was used in an amount of 3.5% by volume, based on the circulation volume of the burning gas, and gas 28 (oxygen-containing inert gas) was used in an amount of 3.8 to 5.7% by volume, based on the circulation volume of the burning gas.

After the above-mentioned operation (ii) for regenerating the catalyst, the catalytic cyclization reaction of a light hydrocarbon feedstock by the same procedure as in the above-mentioned operation (i) and the regeneration of the catalyst by the same procedure as in the above-mentioned operation (ii) were alternately repeated.

Results of the reaction, as obtained in the first catalytic cyclization reaction and the catalytic cyclization reaction using the catalyst which had been regenerated 75 times, are shown in Table 12, together with t he reaction conditions.

The term "GHSV" (gas hourly space velocity) means a value which is determined by the following formula:

$$GHSV\,(\mathrm{hr}^{-1}) = \frac{\text{circulation volume of burning gas (N m}^3\text{/hr)}}{\text{volume of catalyst (m}^3)}$$

EXAMPLE 14

Substantially the same procedure as in Example 13 was repeated, except that makeup gas 27 for use in regenerating the catalyst was used in an amount of 0.1% by volume, based on the circulation volume of the burning gas, and the amount of exhausted burning gas discharged from the burning gas circulation system was 3.9 to 5.8% by volume, based on the circulation volume of the burning gas. Results of the reaction, as obtained in the first catalytic cyclization reaction and the catalytic cyclization reaction using the catalyst which had been regenerated 75 times, are shown in Table 13, together with the reaction conditions.

Comparative Example 12

60 parts by weight of ZSM-5 crystalline alumino-silicate (having an Si/Al atomic ratio of 46 in a zeolite structure thereof) in ammonium ion form, 15 parts by weight of γ-alumina and 25 parts by weight of zinc nitrate were kneaded, and the resultant mixture was subjected to extrusion molding, thereby obtaining a molded product having a diameter of 1.6 mm and a length of 4 to 6 mm. The molded product was dried at 120° C. for 4 hours and then, calcined at 500° C. for 3 hours to obtain a molded ZSM-5 zeolite catalyst having a zinc content of 10% by weight.

Then, a fixed-bed, single-stage, adiabatic reactor was packed with the obtained molded zeolite catalyst to form a catalyst bed. A steam-nitrogen gas mixture containing 80% by volume of steam and having a pressure of 1 kg/cm$^2 \cdot$G and a temperature of 550° C., was fed to and flowed through the reactor for 1 hour to effect a steaming of the zeolite catalyst.

For evaluating the initial-stage catalytic activity of the molded zeolite catalyst thus steamed, the conversion reaction test for n-hexane was conducted using a sample of the zeolite catalyst under isothermal conditions in the same manner as in Example 1. As a result, it was found that the initial stage, first-order reaction rate constant of the decomposition of n-hexane catalyzed by the zeolite catalyst was 3 (sec$^{-1}$).

Then, a 10 mmø quartz reaction tube (isothermal reactor) which was the same as one used in the conversion reaction test for n-hexane was packed with the obtained molded zeolite catalyst to form a catalyst bed, and the quartz reaction tube was externally heated by means of an electric furnace so as to adjust the temperature of the entire catalyst bed evenly to 538° C.

Then, a feedstock was prepared by mixing n-pentane with n-pentene in a weight ratio of 60:40. The obtained feedstock (weight ratio of unsaturated hydrocarbons/saturated hydrocarbons: 0.66) was heated to 538° C. and fed to and flowed through the above-mentioned isothermal reactor under atmospheric pressure, to thereby effect a catalytic cyclization reaction. Results of the reaction, as obtained 5 hours after the start of the reaction, are shown in Table 13, together with the reaction conditions. A diagrammatic view of the reaction apparatus including the quartz reaction tube and the electric furnace is shown in FIG. 8.

As shown in Table 13, in Comparative Example 12, the yield of aromatic hydrocarbons 5 hours after the start of the reaction is high, but the yield of aromatic hydrocarbons 5 days after the start of the reaction is low. That is, in Comparative Example 12, the yield of aromatic hydrocarbons cannot be maintained at a high level for a prolonged period of time.

Comparative Examples 13 to 15

60 parts by weight of ZSM-5 crystalline alumino-silicate (having an Si/Al atomic ratio of 46 in a zeolite structure thereof) in ammonium ion form, 15 parts by weight of γ-alumina and 25 parts by weight of zinc nitrate were kneaded, and the resultant mixture was subjected to extrusion molding, thereby obtaining a molded product having a diameter of 1.6 mm and a length of 4 to 6 mm. The molded product was dried at 120° C. for 4 hours and then, calcined at 500° C. for 3 hours to obtain a molded ZSM-5 zeolite catalyst having a zinc content of 10% by weight.

Then, a fixed-bed, single-stage, adiabatic reactor was packed with the obtained molded zeolite catalyst to form a catalyst bed. A steam-nitrogen gas mixture containing 80% by volume of steam and having a pressure of 1 kg/cm$^2 \cdot$G and a temperature of 700° C., was fed to and flowed through the reactor for 2 hours to effect a steaming of the zeolite catalyst.

For evaluating the initial-stage catalytic activity of the molded zeolite catalyst thus steamed, the conversion reaction test for n-hexane was conducted using a sample of the zeolite catalyst under isothermal conditions in the same manner as in Example 1. As a result, it was found that the initial stage, first-order reaction rate constant of the decomposition of n-hexane catalyzed by the zeolite catalyst was 0.3 (sec$^{-1}$).

Then, a feedstock composed of a $C_5$ fraction (weight ratio of unsaturated hydrocarbons/saturated hydrocarbons: 0.37) indicated in Table 2 was heated to 530° C. and fed to and flowed through the above-mentioned fixed-fed, single-stage adiabatic reactor under atmospheric pressure and at a WHSV of 0.8 hr$^{-1}$, to thereby effect a catalytic cyclization reaction (Comparative Example 13). Results of the reaction, as obtained 5 hours after the start of the reaction, are shown in Table 3, together with the reaction conditions.

Substantially the same procedure as in Comparative Example 13 was repeated except that a feedstock composed only of the saturated hydrocarbons of a $C_5$ fraction indicated in Table 2 was used as the feedstock (Comparative Example 14). Results are shown in Table 13.

As shown in Table 13, the yield of aromatic hydrocarbons (22.9% by weight) obtained in Comparative Example 13 is smaller than the calculated yield of aromatic hydrocarbons (29.8% by weight) which is calculated from the yield of aromatic hydrocarbons in Comparative Example 14 and the yield of aromatic hydrocarbons in Comparative Example 15. The above-mentioned calculated yield of aromatic hydrocarbons can be obtained as follows.

(i) The amount of each component of the $C_5$ fraction (hydrocarbons having 5 or less carbon atoms) indicated in Table 2 is as follows.

| | |
|---|---|
| $C_4H_{10}$ | 0.9% by weight (saturated hydrocarbon) |
| $C_5H_{12}$ | 72.0% by weight (saturated hydrocarbon) |
| $C_5H_{10}$ | 27.1% by weight (unsaturated hydrocarbon) |

(ii) That is, the total amount of the saturated hydrocarbons is 72.9% by weight, and the amount of the unsaturated hydrocarbon is 27.1% by weight.

(iii) As indicated in Table 13, in Comparative Example 14 (only saturated hydrocarbons were used), the yield of aromatic hydrocarbons was 19.7% by weight, and in Comparative Example 15 (only unsaturated hydrocarbons were used), the yield of aromatic hydrocarbons was 56.8% by weight.

(iv) Accordingly, the calculated yield of aromatic hydrocarbons can be calculated by the following formula.

(19.7×72.9+56.8×27.1)/100=29.8% by weight.

TABLE 1

| Components | Composition [% by weight] |
|---|---|
| $C_3H_8$ | 0.1 |
| $C_3H_6$ | 0.6 |
| $C_4H_{10}$ | 24.5 |
| $C_4H_8$ | 74.2 |
| $C_5H_{12}$ | 0.4 |
| $C_5H_{10}$ | 0.2 |

TABLE 2

| Components | Composition [% by weight] |
|---|---|
| $C_3H_8$ | 0.0 |
| $C_3H_6$ | 0.0 |
| $C_4H_{10}$ | 0.9 |
| $C_4H_8$ | 0.0 |
| $C_5H_{12}$ | 72.0 |
| $C_5H_{10}$ | 27.1 |

TABLE 3

Initial stage, first-order reaction rate constant of the decomposition of n-hexane = 0.28 (sec$^{-1}$)

| | Example 1 | | Comparative Example 1 | | Comparative Example 2 | |
|---|---|---|---|---|---|---|
| Reaction conditions | | | | | | |
| Reaction time | 10 hrs | 5 Days | 10 hrs | 5 Days | 10 hrs | 5 Days |
| Pressure [kg/cm$^2$ · G] | 5 | 5 | 5 | 5 | 5 | 5 |
| Weight ratio of unsaturated hydrocarbon/saturated hydrocarbon | 1.54 | 1.54 | 0.37 | 0.37 | 3.00 | 3.00 |
| WHSV [hr$^{-1}$] | 2.8 | 2.8 | 2.8 | 2.8 | 2.8 | 2.8 |
| Inlet temperature of catalyst bed [°C.] | 530.0 | 530.0 | 530.0 | 530.0 | 530.0 | 530.0 |
| Outlet temperature of catalyst bed [°C.] | 550.2 | 545.7 | 469.1 | 470.5 | 593.0 | 515.4 |
| Difference between inlet temperature and outlet temperature of catalyst bed [°C.] | −20.2 | −15.7 | 60.9 | 59.5 | −63.0 | 14.6 |
| Lowest temperature of catalyst bed [°C.] | 530.0 | 514.9 | 469.1 | 470.5 | 530.0 | 514.9 |
| Highest temperature of catalyst bed [°C.] | 554.6 | 554.6 | 530.0 | 530.0 | 592.3 | 530.0 |
| Maximum temperature value [°C.] | 554.6 | 554.6 | 492.0 | — | 586.1 | |
| Composition of reaction product | | | | | | |
| $H_2$ [wt %] | 2.0 | 2.0 | 1.4 | 1.3 | 2.2 | 1.1 |
| $C_1$–$C_3$ hydrocarbons [wt %] | 30.2 | 24.1 | 15.9 | 13.8 | 31.7 | 14.7 |
| $C_4$, $C_5$ hydrocarbons [wt %] | 14.6 | 24.0 | 53.3 | 56.8 | 3.9 | 64.3 |
| $C_6$–$C_8$ aromatic hydrocarbons [wt %] | 49.7 | 46.2 | 26.3 | 25.0 | 60.6 | 19.2 |
| $C_9^+$ aromatic hydrocarbons [wt %] | 2.6 | 2.8 | 2.3 | 2.4 | 1.2 | 0.5 |
| Yield of $C_6$–$C_9$ aromatic hydrocarbons [wt %] | 52.3 | 49.0 | 28.6 | 27.4 | 61.8 | 19.7 |

TABLE 4

Initial stage, first-order reaction rate constant of the decomposition of n-hexane = 0.28 (sec$^{-1}$)

| | Comparative Example 2 | | Example 2 | | Example 3 | |
|---|---|---|---|---|---|---|
| Reaction conditions | | | | | | |
| Reaction time | 10 hrs | 3 Days | 10 hrs | 3 Days | 10 hrs | 3 Days |
| Pressure [kg/cm$^2$ · G] | 5 | 5 | 1 | 1 | 5 | 5 |
| Weight ratio of unsaturated hydrocarbon/saturated hydrocarbon | 3.00 | 3.00 | 3.00 | 3.00 | 3.00 | 3.00 |
| WHSV [hr$^{-1}$] | 2.8 | 2.8 | 2.8 | 2.8 | 2.8 | 2.8 |
| Inlet temperature of catalyst bed [°C.] | 530.0 | 530.0 | 530.0 | 530.0 | 530.0 | 530.0 |
| Outlet temperature of catalyst bed [°C.] | 593.0 | 524.5 | 546.9 | 547.5 | 557.7 | 507.5 |
| Difference between inlet temperature and outlet temperature of catalyst bed [°C.] | −63.0 | 5.5 | −16.9 | −17.5 | −27.7 | 22.5 |
| Lowest temperature of catalyst bed [°C.] | 530.0 | 514.9 | 500.0 | 500.3 | 525.6 | 507.3 |
| Highest temperature of catalyst bed [°C.] | 592.3 | 530.0 | 549.4 | 549.4 | 565.8 | 530.0 |
| Maximum temperature value [°C.] | 586.1 | — | 549.4 | 549.4 | 565.8 | 512.5 |
| Yield of $C_6$–$C_9$ aromatic hydrocarbons [wt %] | 61.8 | 26.1 | 51.1 | 50.5 | 64.5 | 63.5 |

TABLE 5

| | Comp. Ex. 3 | Ex. 4 | Comp. Ex. 4 | Comp. Ex. 5 | Ex. 5 | Comp. Ex. 6 | Comp. Ex. 7 | Comp. Ex. 9 | Comp. Ex. 8 |
|---|---|---|---|---|---|---|---|---|---|
| Pressure = 5[kg/cm² · G]; WHSV = 2.8 [hr⁻¹] | | | | | | | | | |
| Reaction conditions | | | | | | | | | |
| Weight ratio of unsaturated hydrocarbon/saturated hydrocarbon | 0.37 | 1.54 | 3.00 | 0.37 | 1.54 | 3.00 | 0.37 | 1.54 | 3.00 |
| n-hexane decomposition activity*[1][sec⁻¹] | 0.55 | 0.55 | 0.55 | 0.28 | 0.28 | 0.28 | 0.28 | 0.28 | 0.28 |
| Reaction time | 10 hrs | 10 hrs | 10 hrs | 10 hrs | 10 hrs | 10 hrs | 10 hrs | 10 hrs | 10 hrs |
| Inlet temperature of catalyst bed [°C.] | 530 | 530 | 530 | 500 | 500 | 500 | 450 | 450 | 450 |
| Outlet temperature of catalyst bed [°C.] | 468 | 564 | 615 | 458 | 537 | 579 | 438 | 517 | 555 |
| Difference between inlet temperature and outlet temperature of catalyst bed [°C.] | 62 | −34 | −85 | 42 | −37 | −79 | 12 | −67 | −105 |
| Lowest temperature of catalyst bed [°C.] | 468 | 530 | 530 | 458 | 500 | 500 | 428 | 450 | 450 |
| Highest temperature of catalyst bed [°C.] | 530 | 564 | 615 | 500 | 542 | 579 | 451 | 521 | 555 |
| Maximum temperature value [°C.] | — | 555 | 587 | 476 | 542 | 575 | 451 | 521 | — |
| Composition of reaction product | | | | | | | | | |
| $H_2$ [wt %] | 1.4 | 1.9 | 2.0 | 1.1 | 1.8 | 2.0 | 0.9 | 1.6 | 1.8 |
| $C_1$–$C_3$ hydrocarbons [wt %] | 22.6 | 36.0 | 32.7 | 13.9 | 27.8 | 32.0 | 10.7 | 22.7 | 30.1 |
| $C_4$, $C_5$ hydrocarbons [wt %] | 42.7 | 4.8 | 0.9 | 58.2 | 17.2 | 6.2 | 66.1 | 30.5 | 13.0 |
| $C_6$–$C_9$ aromatic hydrocarbons [wt %] | 32.5 | 56.7 | 64.2 | 25.9 | 51.2 | 59.3 | 21.4 | 43.9 | 54.7 |
| Calculated yield of $C_6$–$C_9$ aromatic hydrocarbons [wt %] | — | 54.7*[2] | — | — | 49.3*[3] | — | — | 44.7*[4] | — |
| Yield of aromatic hydrocarbons 5 days after the start of the reaction [wt %] | 26.7 | 49.9 | 32.5 | | | | | | |

*[1] Expressed in terms of initial stage, first-order reaction rate constant of the decomposition of n-hexane
*[2] Calculated by the formula: Yield of aromatic hydrocarbons of Comparative Example 3 × 0.3 + Yield of aromatic hydrocarbons of Comparative Example 4 × 0.7
*[3] Calculated by the formula: Yield of aromatic hydrocarbons of Comparative Example 5 × 0.3 + Yield of aromatic hydrocarbons of Comparative Example 6 × 0.7
*[4] Calculated by the formula: Yield of aromatic hydrocarbons of Comparative Example 7 × 0.3 + Yield of aromatic hydrocarbons of Comparative Example 8 × 0.7

TABLE 6

| | Example 6 | Comparative Example 10 | Example 7 |
|---|---|---|---|
| Reaction conditions | | | |
| n-hexane decomposition activity* [sec⁻¹] | 0.28 | 0.01 | 0.31 |
| Pressure [kg/cm² · G] | 5 | 5 | 5 |
| Weight ratio of unsaturated hydrocarbon/saturated hydrocarbon | 0.86 | 0.86 | 0.86 |
| WHSV [hr⁻¹] | 2.8 | 2.8 | 2.8 |
| Reaction time | 10 hrs | 10 hrs | 10 hrs |
| Inlet temperature of catalyst bed [°C.] | 530.0 | 530.0 | 530.0 |
| Outlet temperature of catalyst bed [°C.] | 512.5 | 523.0 | 512.9 |
| Difference between inlet temperature and outlet temperature of catalyst bed [°C.] | 17.5 | 7.0 | 17.1 |
| Lowest temperature of catalyst bed [°C.] | 511.3 | 502.7 | 512.0 |
| Highest temperature of catalyst bed [°C.] | 530.0 | 530.0 | 530.0 |
| Maximum temperature value [°C.] | 526.0 | — | 525.9 |
| Composition of reaction product | | | |
| $H_2$ [wt %] | 1.8 | 1.4 | 1.8 |
| $C_1$–$C_3$ hydrocarbons [wt %] | 23.4 | 7.4 | 24.5 |
| $C_4$, $C_5$ hydrocarbons [wt %] | 31.6 | 63.6 | 30.0 |
| $C_6$–$C_8$ aromatic hydrocarbons [wt %] | 38.8 | 23.6 | 39.4 |
| $C_9^+$ aromatic hydrocarbons [wt %] | 3.3 | 3.1 | 3.3 |
| Yield of $C_6$–$C_9$ aromatic hydrocarbons [wt %] | 42.1 | 26.7 | 42.7 |

*Expressed in terms of initial stage, first-order reaction rate constant of the decomposition of n-hexane

TABLE 7

| | Example 6 | Comparative Example 11 |
|---|---|---|
| Reaction conditions | | |
| Sodium content [wt ppm] | 110 | 3000 |
| n-hexane decomposition activity* [sec⁻¹] | 0.28 | 0.05 |
| Pressure [kg/cm² · G] | 5 | 5 |
| Weight ratio of unsaturated hydrocarbon/saturated hydrocarbon | 0.86 | 0.86 |
| WHSV [hr⁻¹] | 2.8 | 2.8 |
| Reaction time | 10 hrs | 10 hrs |
| Inlet temperature of catalyst bed [°C.] | 530.0 | 530.0 |
| Outlet temperature of catalyst bed [°C.] | 512.5 | 520.0 |
| Difference between inlet temperature and outlet temperature of catalyst bed [°C.] | 17.5 | 10.0 |
| Lowest temperature of catalyst bed [°C.] | 511.3 | 502.7 |
| Highest temperature of catalyst bed [°C.] | 530.0 | 530.0 |
| Maximum temperature value [°C.] | 526.0 | 526.0 |
| Composition of reaction product | | |
| $H_2$ [wt %] | 1.8 | 1.6 |
| $C_1$–$C_3$ hydrocarbons [wt %] | 23.4 | 9.7 |
| $C_4$, $C_5$ hydrocarbons [wt %] | 31.6 | 54.4 |
| $C_6$–$C_8$ aromatic hydrocarbons [wt %] | 38.8 | 30.3 |
| $C_9^+$ aromatic hydrocarbons [wt %] | 3.3 | 3.2 |
| Yield of $C_6$–$C_9$ aromatic hydrocarbons [wt %] | 42.1 | 33.2 |

*Expressed in terms of initial stage, first-order reaction rate constant of the decomposition of n-hexane

TABLE 8

| | Example 8 |
|---|---|
| Reaction conditions | |
| n-hexane decomposition activity*[1] [sec$^{-1}$] | 0.28 |
| Pressure [kg/cm$^2$ · G] | 5 |
| Weight ratio of unsaturated hydrocarbon/saturated hydrocarbon (based on fresh feed) | 0.86 |
| WHSV [hr$^{-1}$] | 2.8 |
| Reaction time | 10 hrs |
| Inlet temperature of catalyst bed [°C.] | 530.0 |
| Outlet temperature of catalyst bed [°C.] | 494.4 |
| Difference between inlet temperature and outlet temperature of catalyst bed [°C.] | 35.6 |
| Lowest temperature of catalyst bed [°C.] | 494.4 |
| Highest temperature of catalyst bed [°C.] | 530.0 |
| Maximum temperature value [°C.] | 503.2 |
| Yield of C$_6$–C$_9$ aromatic hydrocarbons based on the fresh feed [wt %]*[2] | 50.4 |

*[1] Expressed in terms of initial stage, first-order reaction rate constant of the decomposition of n-hexane
*[2] Yield of C$_6$–C$_9$ aromatic hydrocarbons based on the fresh feed =

$$\frac{\text{The weight of C}_6\text{–C}_9 \text{ aromatic hydrocarbons obtained at the outlet of the reactor}}{\text{The weight of the fresh feed fed to the reactor}} \times 100$$

TABLE 9

| | Example 9 |
|---|---|
| Cyclization reaction conditions | |
| n-hexane decomposition activity*[1] [sec$^{-1}$] | 0.28 |
| Pressure [kg/cm$^2$ · G] | 5 |
| Weight ratio of unsaturated hydrocarbon/saturated hydrocarbon | 0.86 |
| WHSV [hr$^{-1}$] | 2.8 |
| Reaction time | 10 hrs |
| Inlet temperature of catalyst bed [°C.] | 530.0 |
| Outlet temperature of catalyst bed [°C.] | 512.5 |
| Difference between inlet temperature and outlet temperature of catalyst bed [°C.] | 17.5 |
| Lowest temperature of catalyst bed [°C.] | 511.3 |
| Highest temperature of catalyst bed [°C.] | 530.0 |
| Maximum temperature value [°C.] | 526.0 |
| Composition of reaction product | |
| H$_2$ [wt %] | 1.8 |
| C$_1$–C$_3$ hydrocarbons [wt %] | 23.4 |
| C$_4$, C$_5$ hydrocarbons [wt %] | 31.6 |
| C$_6$–C$_8$ aromatic hydrocarbons [wt %] | 38.8 |
| C$_9^+$ aromatic hydrocarbons [wt %] | 3.3 |
| Yield of C$_6$–C$_9$ aromatic hydrocarbons [wt %] | 42.1 |
| Product C comprised mainly of C$_4$–C$_5$ non-aromatic hydrocarbons [wt %] | 21.6 |
| Thermal cracking | |
| COT*[2] [°C.] | 825 |
| COP*[3] [kg/cm$^2$ · G] | 1.06 |
| Steam dilution ratio [—] | 0.35 |
| Yield of product obtained by thermal cracking | |
| Ethylene | 6.2 |
| Propylene | 4.9 |
| C$_4$ fraction | |
| butadiene | 0.7 |
| isobutylene | 0.8 |
| others | 1.9 |
| C$_5$ fraction | 1.0 |
| C$_6$–C$_8$ non-aromatic hydrocarbons | 0.2 |
| C$_6$–C$_8$ aromatic hydrocarbons | 0.8 |
| C$_9^+$ hydrocarbons | 0.1 |
| Others | 5.0 |
| Yield of useful product*[4] [wt %] | 54.7 |

*[1] Expressed in terms of initial stage, first-order reaction rate constant of the decomposition of n-hexane
*[2] COT: Coil Outlet Temperature
*[3] COP: Coil Outlet Pressure

*[4] Yield of useful product =

$$\frac{\text{the total weight of the obtained ethylene, propylene, butadiene and aromatic hydrocarbons}}{\text{the weight of the feedstock fed to the fixed-bed, single-stage, adiabatic reactor}} \times 100$$

TABLE 10

| | Example 10 |
|---|---|
| Cyclization reaction conditions | |
| n-hexane decomposition activity* [sec$^{-1}$] | 0.28 |
| Pressure [kg/cm$^2$ · G] | 5 |
| Weight ratio of unsaturated hydrocarbon/saturated hydrocarbon | 0.86 |
| WHSV [hr$^{-1}$] | 2.8 |
| Reaction time | 10 hrs |
| Inlet temperature of catalyst bed [°C.] | 530.0 |
| Outlet temperature of catalyst bed [°C.] | 512.5 |
| Difference between inlet temperature and outlet temperature of catalyst bed [°C.] | 17.5 |
| Lowest temperature of catalyst bed [°C.] | 511.3 |
| Highest temperature of catalyst bed [°C.] | 530.0 |
| Maximum temperature value [°C.] | 526.0 |
| Composition of reaction product | |
| H$_2$ [wt %] | 1.8 |
| C$_1$–C$_3$ hydrocarbons [wt %] | 23.4 |
| C$_4$, C$_5$ hydrocarbons [wt %] | 31.6 |
| C$_6$–C$_8$ aromatic hydrocarbons [wt %] | 38.8 |
| C$_9^+$ aromatic hydrocarbons [wt %] | 3.3 |
| Yield of C$_6$–C$_9$ aromatic hydrocarbons [wt %] | 42.1 |
| Yield of benzene obtained by dealkylation reaction [wt %/Feed] | 30.9 |

*Expressed in terms of initial stage, first-order reaction rate constant of the decomposition of n-hexane

TABLE 11

| | | | Example 11 | Example 12 |
|---|---|---|---|---|
| Dealumination | | | | |
| Reaction conditions | First-stage | Temperature of fed steam [°C.] | 600 | 600 |
| | | Steam partial pressure [kg/cm$^2$] | 0.8 | 0.8 |
| | | Steaming time [min] | 10 | 60 |
| | Second-stage | Temperature of fed steam [°C.] | 640 | — |
| | | Steam partial pressure [kg/cm$^2$] | 0.8 | — |
| | | Steaming time [min] | 14 | — |
| *[1] Average temperature of uppermost part of catalyst bed [°C.] | | | 656.9 | 614.4 |
| Average temperature of lowermost part catalyst bed [°C.] | | | 661.1 | 651.5 |
| Difference between average temperatures [°C.] | | | 4.2 | 37.1 |
| Catalytic activity | | | | |
| n-hexane decomposition activity*[2] of uppermost part of catalyst bed | | | 0.52 | 0.74 |
| n-hexane decomposition activity of middle part of catalyst bed | | | 0.48 | 0.45 |
| n-hexane decomposition activity of lowermost part of catalyst bed | | | 0.48 | 0.45 |

TABLE 11-continued

|  | Example 11 | Example 12 |
|---|---|---|
| Average n-hexane decomposition activity of all parts of catalyst bed | 0.50 | 0.50 |
| Cyclization reaction conditions | | |
| Pressure [kg/cm$^2$ · G] | 5 | 5 |
| Weight ratio of unsaturated hydrocarbon/saturated hydrocarbon | 0.86 | 0.86 |
| WHSV [hr$^{-1}$] | 2.8 | 2.8 |
| Reaction time | 10 hrs | 10 hrs |
| Inlet temperature of catalyst bed [°C.] | 530.0 | 530.0 |
| Outlet temperature of catalyst bed [°C.] | 514.6 | 516.1 |
| Difference between inlet temperature and outlet temperature of catalyst bed [°C.] | 15.4 | 13.9 |
| Lowest temperature of catalyst bed [°C.] | 512.0 | 512.0 |
| Highest temperature of catalyst bed [°C.] | 530.0 | 530.0 |
| Maximum temperature value [°C.] | 526.0 | 526.0 |
| Composition of reaction product | | |
| H$_2$ [wt %] | 1.7 | 1.7 |
| C$_1$–C$_3$ hydrocarbons [wt %] | 27.7 | 29.6 |
| C$_4$, C5 hydrocarbons [wt %] | 25.2 | 22.4 |
| C$_6$–C$_8$ aromatic hydrocarbons [wt %] | 42.0 | 42.1 |
| C$_9$$^+$ aromatic hydrocarbons [wt %] | 3.2 | 3.2 |
| Yield of C$_6$–C$_9$ aromatic hydrocarbons [wt %] | 45.2 | 45.3 |
| Relative amount of coke formed on uppermost part of catalyst bed | 1 | 1.7 |

*[1)]In Example 11, each of the average temperatures is an average of all data obtained in first- and second-stages.
*[2)]Expressed in terms of initial stage, first-order reaction rate constant of the decomposition of n-hexane

TABLE 12

|  | Example 13 | | Example 14 | |
|---|---|---|---|---|
|  | First cyclization reaction | Catalyst regenerated 75 times | First cyclization reaction | Catalyst regenerated 75 times |
| Reaction conditions | | | | |
| n-hexane decomposition activity* [sec$^{-1}$] | 0.28 | 0.28 | 0.28 | 0.28 |
| Pressure [kg/cm$^2$ · G] | 5 | 5 | 5 | 5 |
| Weight ratio of unsaturated hydrocarbon/saturated hydrocarbon | 0.86 | 0.86 | 0.86 | 0.86 |
| WHSV [hr$^{-1}$] | 2.8 | 2.8 | 2.8 | 2.8 |
| Reaction time | 10 hrs | 10 hrs | 10 hrs | 10 hrs |
| Inlet temperature of catalyst bed [°C.] | 530.0 | 550.0 | 530.0 | 550.0 |
| Outlet temperature of catalyst bed [°C.] | 512.5 | 519.43 | 512.5 | 522.4 |
| Difference between inlet temperature and outlet temperature of catalyst bed [°C.] | 17.5 | 30.6 | 17.5 | 27.6 |
| Lowest temperature of catalyst bed [°C.] | 511.3 | 517.1 | 511.3 | 515.5 |
| Highest temperature of catalyst bed [°C.] | 530.0 | 550.0 | 530.0 | 550.0 |
| Maximum temperature value [°C.] | 526.0 | 534.8 | 526.0 | 534.8 |
| Composition of reaction product | | | | |
| H$_2$ [wt %] | 1.8 | 1.9 | 1.8 | 1.8 |
| C$_1$–C$_3$ hydrocarbons [wt %] | 23.4 | 18.5 | 23.4 | 13.7 |
| C$_4$, C$_5$ hydrocarbons [wt %] | 31.6 | 37.2 | 31.6 | 46.2 |
| C$_6$–C$_8$ aromatic hydrocarbons [wt %] | 38.8 | 39.2 | 38.8 | 34.1 |
| C$_9$$^+$ aromatic hydrocarbons [wt %] | 3.3 | 2.9 | 3.3 | 3.1 |
| Yield of C$_6$–C$_9$ aromatic hydrocarbons [wt %] | 42.1 | 42.1 | 42.1 | 37.2 |

*Expressed in terms of initial stage, first-order reaction rate constant of the decomposition of n-hexane

TABLE 13

|  | Comp. Ex. 12 | Comp. Ex. 13 | Comp. Ex. 14 | Comp. Ex. 15 |
|---|---|---|---|---|
| Reaction conditions | | | | |
| Pressure [kg/cm$^2$ · G] | 0 | 0 | 0 | 0 |
| Weight ratio of unsaturated hydrocarbon/saturated hydrocarbon | 0.66 | 0.37 | see *[2)] | see *[3)] |
| n-hexane decomposition activity*[1)] [sec$^{-1}$] | 3 | 0.3 | 0.3 | 0.3 |

TABLE 13-continued

|  | Comp. Ex. 12 | Comp. Ex. 13 | Comp. Ex. 14 | Comp. Ex. 15 |
|---|---|---|---|---|
| Reaction time | 5 hrs | 5 hrs | 5 hrs | 5 hrs |
| Inlet temperature of catalyst bed [°C.] | 538 | 530 | 530 | 530 |
| Outlet temperature of catalyst bed [°C.] | 538 | 434 | 413 | 528 |
| Difference between inlet temperature and outlet temperature of catalyst bed [°C.] | — | 96 | 117 | 2 |
| Lowest temperature of catalyst bed [°C.] | — | 434 | 413 | 404 |
| Highest temperature of catalyst bed [°C.] | — | 530 | 530 | 530 |
| Maximum temperature value [°C.] | — | — | — | — |
| $C_6$–$C_9$ aromatic hydrocarbons [wt %] | 62.1 | 22.9 | 19.7 | 56.8 |
| Calculated yield of $C_6$–$C_9$ aromatic hydrocarbons [wt %] | — | 29.8 | — | — |
| Yield of aromatic hydrocarbons 5 days after the start of the reaction [wt %] | 4.0 | 21.8 | 18.8 | 4.3 |

*[1]Expressed in terms of initial stage, first-order reaction rate constant of the decomposition of n-hexane
*[2]Only saturated hydrocarbons of $C_5$ fraction indicated in Table 2 were used
*[3]Only unsaturated hydrocarbons of $C_5$ fraction indicated in Table 2 were used

INDUSTRIAL APPLICABILITY

By the method of the present invention, not only can aromatic hydrocarbons be produced in high yield from light hydrocarbons comprising olefins and/or paraffins, but also the lowering of the catalytic activity is small, so that the production of aromatic hydrocarbons can be stably conducted for a prolonged period of time, using a fix-bed, adiabatic reactor which can be commercially advantageously employed in view of the simple structure and high efficiency thereof. The method of the present invention can be widely, advantageously used in the petrochemical industry and in petroleum refining, especially in the production of aromatic compounds and high-octane gasolines.

We claim:

1. A method for producing aromatic hydrocarbons from light hydrocarbons by catalytic cyclization, which comprises supplying a light hydrocarbon feedstock comprising a saturated hydrocarbon fraction and an unsaturated hydrocarbon fraction, and wherein the weight ratio of said saturated hydrocarbon fraction to said unsaturated hydrocarbon fraction is from 0.43 to 2.33 to a fixed-bed, adiabatic reactor containing a fixed catalyst bed comprised of a zeolite catalyst, to thereby contact the light feedstock with said zeolite catalyst in said fixed-bed, adiabatic reactor and effect a catalytic cyclization reaction of said light hydrocarbon feedstock, said zeolite catalyst being at least one member selected from the group consisting of a substantially fresh zeolite catalyst and a steamed zeolite catalyst, wherein said catalytic cyclization reaction is performed under conditions which satisfy all the following requirements (1), (2), (3) and (4):

(1) said zeolite catalyst has an initial stage-catalytic activity of 0.2 ($sec^{-1}$) or more in terms of the initial stage, first-order reaction rate constant of the decomposition of n-hexane catalyzed by the zeolite catalyst as measured at a temperature of 500° C. under atmospheric pressure;

(2) the catalyst bed has a temperature in the range of from 450° C. to 650° C.;

(3) the catalyst bed exhibits a temperature distribution with respect to the distance from an inlet of the catalyst bed to an outlet of the catalyst bed, wherein said temperature distribution has at least one maximum temperature value between the inlet and the outlet of the catalyst bed; and (4) the temperature of the outlet of the catalyst bed is in the range of ±40° C. relative to the temperature of the inlet of the catalyst bed.

2. The method according to claim 1, wherein said zeolite catalyst consists essentially of a zeolite.

3. The method according to claim 1, wherein said zeolite catalyst comprises a mixture of a zeolite and at least one member selected from the group consisting of a metal belonging to Group VIII, Ib, IIb or IIId of the Periodic Table and compounds thereof.

4. The method according to claim 3, wherein said zeolite catalyst comprises a mixture of a zeolite and at least one member selected from the group consisting of zinc and compounds thereof.

5. The method according to claim 4, wherein said zeolite catalyst comprises a mixture of a zeolite, at least one member selected from the group consisting of zinc and compounds thereof, and alumina.

6. The method according to claim 4, wherein said zeolite catalyst comprises a mixture of a zeolite and a product obtained by heat-treating in steam a mixture of alumina and at least one member selected from the group consisting of zinc and compounds thereof.

7. The method according to claim 4, wherein said zeolite catalyst comprises a mixture of a zeolite and zinc aluminate.

8. The method according to claim 4, wherein the content of said at least one member selected from the group consisting of zinc and compounds thereof in said zeolite catalyst is from 5 to 25% by weight in terms of the amount of zinc.

9. The method according to claim 1, wherein said zeolite of said zeolite catalyst is substituted with a metal belonging to Group VIII, Ib, IIb or IIIa of the Periodic Table.

10. The method according to claim 9, wherein said metal is zinc and the content of zinc in said zeolite catalyst is 5 to 25% by weight.

11. The method according to any one of claims 1 to 10, wherein the zeolite of said zeolite catalyst has an Si/Al atomic ratio of at least 12 in the zeolite structure thereof, and has a sodium content of 500 ppm by weight or less.

12. The method according to any one of claims 1 to 10, wherein said zeolite catalyst comprises a ZSM-5 zeolite.

13. The method according to any one of claims 1 to 10, wherein said zeolite catalyst is a substantially fresh zeolite catalyst.

14. The method according to any one of claims 1 to 10, wherein said zeolite catalyst is a steamed zeolite catalyst which is obtained by steaming a substantially fresh zeolite catalyst.

15. The method according to claim 1, wherein said zeolite catalyst comprises a mixture of a steamed zeolite catalyst which has been obtained by steaming a substantially fresh zeolite catalyst consisting essentially of a zeolite, and at least one member selected from the group consisting of a metal belonging to Group VIII, Ib, IIb or IIIa of the Periodic Table and compounds thereof.

16. The method according to claim 14, wherein the steaming of said substantially fresh zeolite catalyst is performed by flowing steam through a steaming reactor containing said substantially fresh zeolite catalyst in a sequence of the following steps (a) and (b):

(a) flowing steam having a steam partial pressure of at least 0.1 kg/cm$^2$ and a temperature of from 500° to 650° C. through said steaming reactor, to thereby contact said substantially fresh zeolite catalyst with the steam for 0.1 to 3 hours; and (b) temporarily stopping the flow of steam through said steaming reactor and removing the steam which remains in said reactor, whereupon steam having a steam partial pressure of 0.1 to 10 kg/cm$^2$ and a temperature of from 515° to 700° C. is flowed through said steaming reactor, with the proviso that the temperature of the steam flowed in step (b) is higher than the temperature of the steam flowed in step (a), wherein said step (b) is performed at least once, so that the steam individually flowed in the or each step (b) is brought into contact with said zeolite catalyst which has been steamed in the step preceding the or each step (b).

17. The method according to claim 16, wherein said substantially fresh zeolite catalyst comprises a ZSM-5 zeolite.

18. The method according to claim 1, wherein said light hydrocarbon feedstock comprises at least one member selected from the group consisting of a $C_4$ fraction of a product from a high temperature-thermal cracking system of a petroleum hydrocarbon, a fraction obtained by removing butadiene from said $C_4$ fraction, a fraction obtained by removing butadiene and i-butene from said $C_4$ fraction, a $C_5$ fraction of a product from a high temperature-thermal cracking system of a petroleum hydrocarbon, a fraction obtained by removing dienes from said $C_5$ fraction, thermally-cracked gasoline, a raffinate obtained by extracting aromatic hydrocarbons from thermally-cracked gasoline, fluid catalytic cracking (FCC)-produced liquefied petroleum gas (LPG), FCC-cracked gasoline, a raffinate obtained by extracting aromatic hydrocarbons from reformate, coker LPG and virgin naphtha.

19. The method according to claim 1, wherein the internal pressure of said adiabatic reactor during the cyclization reaction is in the range of from atmospheric pressure to 30 kg/cm$^2$·G, and said light hydrocarbon feedstock is fed to said adiabatic reactor at a weight hourly space velocity (WHSV) of 0.1 to 50 hr$^{-1}$.

20. The method according to claim 1, which further comprises separating the resultant cyclization reaction mixture containing an aromatic hydrocarbon product into product A comprised mainly of the aromatic hydrocarbon product and product B comprised mainly of hydrogen and a non-aromatic hydrocarbon product having 1 to 5 carbon atoms, and wherein said separation is performed by means of a gas-liquid separator and optionally a distillation column.

21. The method according to claim 1, which further comprises separating the resultant cyclization reaction mixture containing an aromatic hydrocarbon product into product A comprised mainly of the aromatic hydrocarbon product, product C comprised mainly of a non-aromatic hydrocarbon product having 4 to 5 carbon atoms and product D comprised mainly of hydrogen and a non-aromatic hydrocarbon product having 1 to 3 carbon atoms, and wherein said separation is performed by means of a gas-liquid separator and optionally a distillation column.

22. The method according to claim 20 or 21, wherein said gas-liquid separation is conducted using a coolant comprised of propylene or ethylene, and wherein said propylene or said ethylene is produced in and used as a coolant in a process for producing ethylene by a high temperature-thermal cracking of a petroleum hydrocarbon.

23. The method according to claim 20, wherein at least part of said product B comprised mainly of hydrogen and a non-aromatic hydrocarbon product having 1 to 5 carbon atoms is recycled to said adiabatic reactor and is used as a part of said light hydrocarbon feedstock.

24. The method according to claim 20, wherein at least part of said product B comprised mainly of hydrogen and a non-aromatic hydrocarbon product having 1 to 5 carbon atoms is supplied to a high temperature-thermal cracking system of a petroleum hydrocarbon material.

25. The method according to claim 21, wherein at least part of at least one member selected from the group consisting of said product C comprised mainly of a non-aromatic hydrocarbon product having 4 to 5 carbon atoms and said product D comprised mainly of hydrogen and a non-aromatic hydrocarbon product having 1 to 3 carbon atoms is recycled to said adiabatic reactor and is used as a part of said light hydrocarbon feedstock.

26. The method according to claim 21, wherein at least part of at least one member selected from the group consisting of said product C comprised mainly of a non-aromatic hydrocarbon product having 4 to 5 carbon atoms and said product D comprised mainly of hydrogen and a non-aromatic hydrocarbon product having 1 to 3 carbon atoms is supplied to a high temperature-thermal cracking system of a petroleum hydrocarbon.

27. The method according to claim 20 or 21, which further comprises processing said product A comprised mainly of the aromatic hydrocarbon product by at least one method selected from the group consisting of the following methods:

a method in which said product A is processed using a dealkylation apparatus to thereby produce benzene;

a method in which said product A is processed using a distillation apparatus, an extraction apparatus or an extractive distillation apparatus to thereby produce benzene, toluene and xylene;

a method in which said product A is processed using a disproportionation apparatus or an isomerization apparatus; and a method in which said product A is blended with gasoline.

28. The method according to any one of claims 1 to 10, which further comprises temporarily stopping the supply of said light hydrocarbon feedstock to the fixed-bed, adiabatic reactor, and burning off coke formed on said zeolite catalyst during the catalytic cyclization reaction with an oxygen-containing inert gas as a burning gas to regenerate the zeolite catalyst in a catalyst regeneration zone.

29. The method according to claim 28, wherein an exhausted burning gas flowing out of said catalyst regeneration zone is recycled to said catalyst regeneration zone through a heater by means of a recycling compressor to thereby form a burning gas circulation system comprising said catalyst regeneration zone, said recycling compressor and said heater which are connected in this order through a pipeline, and wherein a fresh, oxygen-containing inert gas is supplied to the burning gas circulation system at a first port positioned between an outlet of the catalyst regeneration zone and an inlet of the heater in an amount of 0.05 to 50% by volume, based on the circulation volume of the burning gas, while discharging from said burning gas circulation system the exhausted burning gas flowing out of the catalyst regeneration zone before reaching the heater in an amount which is substantially equal to the amount of said fresh, oxygen-containing inert gas supplied to said first port, wherein the amount and oxygen content of said fresh, oxygen-containing inert gas supplied are adjusted, so that the burning gas flowing into the catalyst regeneration zone has an oxygen content of 0.01 to 10% by volume.

30. The method according to claim 29, which further comprises supplying a fresh inert gas containing no oxygen to said burning gas circulation system at a second port, which is identical with said first port or is provided separately from said first port between the outlet of the catalyst regeneration zone and the inlet of the heater, in an amount of 10% by volume or less, based on the circulation volume of the burning gas, while incrementally discharging from said burning gas circulation system said exhausted burning gas flowing out of the catalyst regeneration zone before reaching the heater in an amount which is substantially equal to the amount of said fresh inert gas, containing no oxygen, supplied to said second port, thereby suppressing an increase in the partial pressure of steam in the burning gas flowing into the catalyst regeneration zone.

31. The method according to claim 30, which further comprises cooling the burning gas to be compressed by means of the recycling compressor, and heating the compressed burning gas before reaching the heater, wherein said cooling and heating are conducted by means of at least one heat exchanger.

32. The method according to claim 14, wherein the steaming of said substantially fresh zeolite catalyst is performed using a steam circulation system including a steaming reactor, a recycling compressor, a heater and at least one heat exchanger, which are connected through a pipeline.

33. The method according to claim 32, wherein said steaming reactor is used as said adiabatic reactor.

34. The method according to claim 16, wherein the steaming of said substantially fresh zeolite catalyst is performed using a steam circulation system including a steaming reactor, a recycling compressor, a heater and at least one heat exchanger, which are connected through a pipeline.

35. The method according to claim 34, wherein said steaming reactor is used as said adiabatic reactor.

36. The method according to claim 14, wherein the steaming of said substantially fresh zeolite catalyst is performed using a steam circulation system including a steaming reactor, a recycling compressor, a heater and at least one heat exchanger, which are connected through a pipeline, and which further comprises temporarily stopping the supply of said light hydrocarbon feedstock to the fixed-bed, adiabatic reactor, and burning off coke formed on said zeolite catalyst during the catalytic cyclization reaction with an oxygen containing inert gas as a burning gas to regenerate the zeolite catalyst in a catalyst regeneration zone, wherein an exhausted burning gas flowing out of said catalyst regeneration zone is recycled to said catalyst regeneration zone through a heater by means of a recycling compressor to thereby form a burning gas circulation system comprising said catalyst regeneration zone, said recycling compressor and said heater, which are connected in this order through a pipeline, and wherein a fresh, oxygen-containing inert gas is supplied to the burning gas circulation system at a first port positioned between an outlet of the catalyst regeneration zone and an inlet of the heater in an amount of 0.05 to 50% by volume, based on the circulation volume of the burning gas, while discharging from said burning gas circulation system the exhausted burning gas flowing out of the catalyst regeneration zone before reaching the heater in an amount which is substantially equal to the amount of said fresh, oxygen-containing inert gas supplied to said first port, wherein the amount and oxygen content of said fresh, oxygen-containing inert gas supplied are adjusted, so that the burning gas flowing into the catalyst regeneration zone has an oxygen content of 0.01 to 10% by volume, and wherein said steam circulation system is utilized as the burning gas circulation system for the regeneration of said zeolite catalyst, wherein said steaming reactor is used as or replaced by a regeneration reactor comprising the catalyst regeneration zone in the burning gas circulation system, and wherein the burning gas for the burning gas circulation system is used in place of the steam for the steam circulation system.

37. The method according to claim 36, wherein said steaming reactor is used as said adiabatic reactor and as said regeneration reactor.

38. The method according to claim 16, wherein the steaming of said substantially fresh zeolite catalyst is performed using a steam circulation system including a steaming reactor, a recycling compressor, a heater and at least one heat exchanger, which are connected through a pipeline, and which further comprises temporarily stopping the supply of said light hydrocarbon feedstock to the fixed-bed, adiabatic reactor, and burning off coke formed on said zeolite catalyst during the catalytic cyclization reaction with an oxygen containing inert gas as a burning gas to regenerate the zeolite catalyst in a catalyst regeneration zone, wherein an exhausted burning gas flowing out of said catalyst regeneration zone is recycled to said catalyst regeneration zone through a heater by means of a recycling compressor to thereby form a burning gas circulation system comprising said catalyst regeneration zone, said recycling compressor and said heater, which are connected in this order through a pipeline, and wherein a fresh, oxygen-containing inert gas is supplied to the burning gas circulation system at a first port positioned between an outlet of the catalyst regeneration zone and an inlet of the heater in an amount of 0.05 to 50% by volume, based on the circulation volume of the burning gas, while discharging from said burning gas circulation system the exhausted burning gas flowing out of the catalyst regeneration zone before reaching the heater in an amount which is substantially equal to the amount of said fresh, oxygen-containing inert gas supplied to said first port, wherein the amount and oxygen content of said fresh, oxygen-containing inert gas supplied are adjusted, so that the burning gas flowing into the catalyst regeneration zone has an oxygen content of 0.01 to 10% by volume, and wherein said steam circulation system is utilized as the burning gas circulation system for the regeneration of said zeolite catalyst, wherein said steaming reactor is used as or replaced by a regeneration reactor comprising the catalyst regeneration zone in the burning gas circulation system, and wherein the burning gas for the burning gas circulation system is used in place of the steam for the steam circulation system.

39. The method according to claim 38, wherein said steaming reactor is used as said adiabatic reactor and as said regeneration reactor.

* * * * *